US012350037B2

(12) United States Patent
Georgeson et al.

(10) Patent No.: US 12,350,037 B2
(45) Date of Patent: Jul. 8, 2025

(54) ERGONOMICS IMPROVEMENT SYSTEMS HAVING WEARABLE SENSORS AND RELATED METHODS

(71) Applicant: The Boeing Company, Chicago, IL (US)

(72) Inventors: Gary E. Georgeson, Tacoma, WA (US); Saman Farhangdoust, Miami, FL (US)

(73) Assignee: The Boeing Company, Arlington, VA (US)

( * ) Notice: Subject to any disclaimer, the term of this patent is extended or adjusted under 35 U.S.C. 154(b) by 324 days.

(21) Appl. No.: 17/383,179

(22) Filed: Jul. 22, 2021

(65) Prior Publication Data

US 2023/0032821 A1 Feb. 2, 2023

(51) Int. Cl.
*A61B 5/11* (2006.01)
*A61B 5/00* (2006.01)

(52) U.S. Cl.
CPC .......... *A61B 5/1126* (2013.01); *A61B 5/1122* (2013.01); *A61B 5/4576* (2013.01); *A61B 5/458* (2013.01); *A61B 5/6807* (2013.01); *A61B 5/6823* (2013.01); *A61B 5/6824* (2013.01); *A61B 5/6825* (2013.01); *A61B 5/7405* (2013.01); *A61B 5/7455* (2013.01); *A61B 5/746* (2013.01); *A61B 2503/20* (2013.01);
(Continued)

(58) Field of Classification Search
CPC ... A61B 5/1126; A61B 5/1122; A61B 5/4576; A61B 5/458; A61B 5/6807; A61B 5/6823; A61B 5/6824; A61B 5/6825; A61B 5/7405; A61B 5/7455; A61B 5/746; A61B 2503/20; A61B 2562/0247; A61B 2562/0252; A61B 5/459
See application file for complete search history.

(56) References Cited

U.S. PATENT DOCUMENTS

| | | |
|---|---|---|
| 6,110,130 A | 8/2000 | Kramer |
| 7,090,576 B2 | 8/2006 | Herbrich et al. |
| 9,358,426 B2 | 6/2016 | Aragones et al. |

(Continued)

FOREIGN PATENT DOCUMENTS

| | | |
|---|---|---|
| CA | 3167763 A1 | 1/2023 |
| CN | 109984747 A | 7/2019 |

(Continued)

OTHER PUBLICATIONS

European Patent Office, "Extended European Search Report", issued in connection with application No. 22183800.6 on Jan. 17, 2023, 18 pages.

(Continued)

*Primary Examiner* — Matthew Kremer
*Assistant Examiner* — Jonathan M Haney
(74) *Attorney, Agent, or Firm* — Hanley, Flight & Zimmerman, LLC

(57) ABSTRACT

Wearable ergonomics improvement systems and related methods are disclosed. An example ergonomics improvement system includes a membrane including a first frame having a plurality of first cutouts defining a first pattern. The system includes a sensor coupled to the membrane and includes a second frame having a plurality of second cutouts defining a second pattern. The first pattern is complementary to the second pattern.

17 Claims, 14 Drawing Sheets

(52) U.S. Cl.
CPC ............... *A61B 2562/0247* (2013.01); *A61B 2562/0252* (2013.01)

(56) References Cited

U.S. PATENT DOCUMENTS

| | | | |
|---|---|---|---|
| 9,610,036 | B1 | 4/2017 | De Sapio et al. |
| 10,065,074 | B1 | 9/2018 | Hoang et al. |
| 10,838,373 | B2 | 11/2020 | Arrowood et al. |
| 11,783,495 | B1 | 10/2023 | Messmore et al. |
| 11,918,855 | B2 | 3/2024 | Georgeson et al. |
| 2001/0020140 | A1 | 9/2001 | Kramer |
| 2003/0163287 | A1* | 8/2003 | Vock ............... H04M 1/72412 702/187 |
| 2004/0188618 | A1* | 9/2004 | Hamamoto ............ G01J 5/10 250/338.1 |
| 2013/0217352 | A1 | 8/2013 | Pan et al. |
| 2016/0015972 | A1* | 1/2016 | Hyde ................ A61B 5/0022 607/48 |
| 2016/0334762 | A1 | 11/2016 | Arrowood et al. |
| 2016/0335574 | A1 | 11/2016 | Arrowood et al. |
| 2017/0188894 | A1* | 7/2017 | Chang ............... A61B 5/1121 |
| 2018/0279919 | A1 | 10/2018 | Bansbach et al. |
| 2018/0369637 | A1 | 12/2018 | Hoang et al. |
| 2019/0103033 | A1 | 4/2019 | Lu Hill |
| 2019/0168120 | A1 | 6/2019 | Cossairt |
| 2020/0046261 | A1* | 2/2020 | Rustamova .......... A61B 5/4576 |
| 2020/0051446 | A1 | 2/2020 | Rubinstein |
| 2020/0205673 | A1* | 7/2020 | Yi ..................... A61B 5/389 |
| 2020/0218974 | A1 | 7/2020 | Cheng et al. |
| 2020/0276501 | A1 | 9/2020 | Crossairt et al. |
| 2020/0281508 | A1 | 9/2020 | Ren |
| 2020/0327465 | A1* | 10/2020 | Baek ................ G16H 50/30 |
| 2020/0401224 | A1* | 12/2020 | Cotton ............... A61B 5/742 |
| 2021/0008413 | A1 | 1/2021 | Asikainen |
| 2021/0315488 | A1 | 10/2021 | McDaid |
| 2022/0003577 | A1 | 1/2022 | Evke et al. |
| 2022/0287651 | A1 | 9/2022 | Projetti |
| 2022/0374083 | A1 | 11/2022 | Tajima et al. |
| 2022/0378349 | A1 | 12/2022 | Slepian |
| 2023/0021704 | A1 | 1/2023 | Georgeson |
| 2023/0032821 | A1 | 2/2023 | Georgeson |
| 2023/0065631 | A1 | 3/2023 | Laughlin |
| 2023/0069316 | A1 | 3/2023 | Laughlin et al. |
| 2023/0298760 | A1 | 9/2023 | Wagner |

FOREIGN PATENT DOCUMENTS

| | | |
|---|---|---|
| IT | 201900002215 | 8/2020 |
| JP | 2012183291 | 9/2012 |
| WO | 2019112737 A1 | 6/2019 |
| WO | 2020102527 | 5/2020 |
| WO | 2021077093 A1 | 4/2021 |
| WO | 2021095493 A1 | 5/2021 |

OTHER PUBLICATIONS

Baldwin et al., "Kirigami Strain Sensors Microfabricated From Thin-Film Parylene C", Journal of Microelectromechanical Systems, vol. 2, No. 6, Dec. 2018, 7 pages.

Wang et al., "Topological design of carbon nanotube-based nanocomposites for strain sensing" Behavior and Mechanics of Multifunctional Materials XIII, Mar. 29, 2019, 9 pages.

Groeger et al., "LASEC: Instant Fabrication of Stretchable Circuits Using a Laser Cutter", CHI '19: Proceedings of the 2019 CHI Conference on Human Factors in Computing Systems, May 2019, 14 pages.

Farhangdoust et al., "Auxetic MEMS Sensor", Proceedings vol. 11379, Sensors and Smart Structures Technologies for Civil, Mechanical, and Aerospace Systems 2020, Apr. 23, 2020, 10 pages.

Hara et al., "Human Movement Instruction System that Utilizes Avatar Overlays Using Stereoscopic Images," WSCG, published in 2000, 8 pages.

Pinho, "The Use of Thermal Infra-red Imaging to Reveal Muscle Injuries Caused by Physically Demanding Jobs in Industrial Operations," Faculdade de Engenharia da Universidade do Porto, Sep. 2016, 119 pages.

Rammer et al., "Assessment of a markerless motion analysis system for manual wheelchair application," 2018, Journal of NeuroEngineering and Rehabilitation, pp. 1-12, 13 pages.

United States Patent Office, "Non-Final Office Action," issued in connection with U.S. Appl. No. 17/412,038, dated Oct. 25, 2023, 20 pages.

European Patent Office, "Extended European Search Report," issued in connection with European Patent Application No. 22183797.4 on Dec. 9, 2022, 8 pages.

European Patent Office, "Extended European Search Report," issued in connection with European Patent Application No. 22190359.4 on Jan. 19, 2023, 8 pages.

European Patent Office, "Extended European Search Report," issued in connection with European Patent Application No. 22190357.8 on Jan. 30, 2023, 8 pages.

United States Patent Office, "Non-Final Office Action," issued in connection with U.S. Appl. No. 17/383,173, dated Sep. 8, 2023, 8 pages.

United States Patent Office, "Notice of Allowance" issued in connection with U.S. Appl. No. 17/383,173, dated Oct. 26, 2023, 5 pages.

United States Patent and Trademark Office, "Notice of Allowance," issued in connection with U.S. Appl. No. 17/383,173, dated Jan. 11, 2024, 2 pages.

Canadian Intellectual Property Office, "Requisition by Examiner," issued in connection with Canadian Application No. 3170483, dated Feb. 20, 2024, 3 pages.

United States Patent and Trademark Office, "Final Rejection," issued in connection with U.S. Appl. No. 17/412,038, dated Mar. 22, 2024, 13 pages.

Canadian Intellectual Property Office, "Requisition by Examiner," issued in connection with Canadian Patent Application No. 3,167,763, dated Nov. 27, 2024, 5 pages.

United States Patent and Trademark Office, "Non-Final Office Action," issued in connection with U.S. Appl. No. 17/412,049, dated Mar. 3, 2025, 25 pages.

* cited by examiner

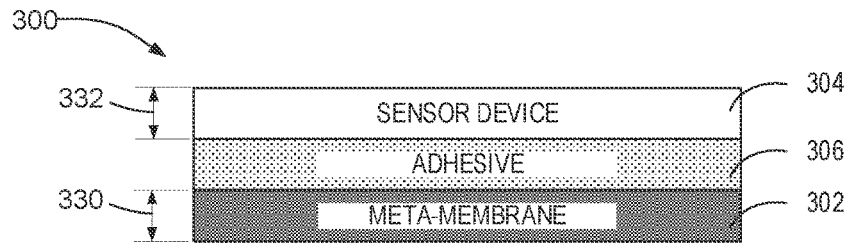
FIG. 3A
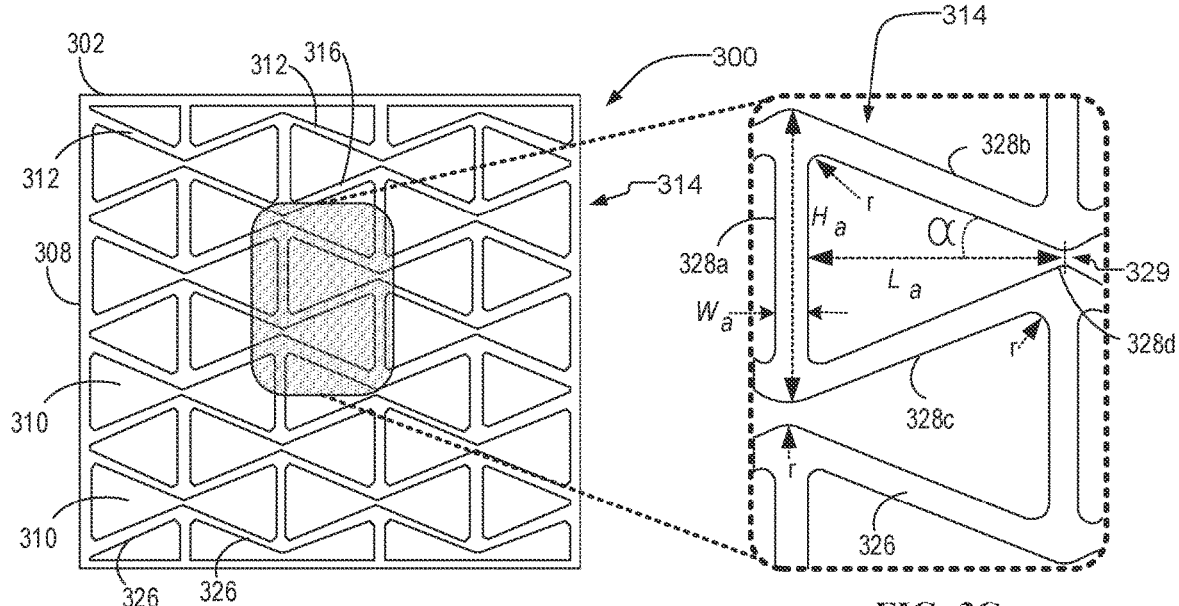
FIG. 3B
FIG. 3C
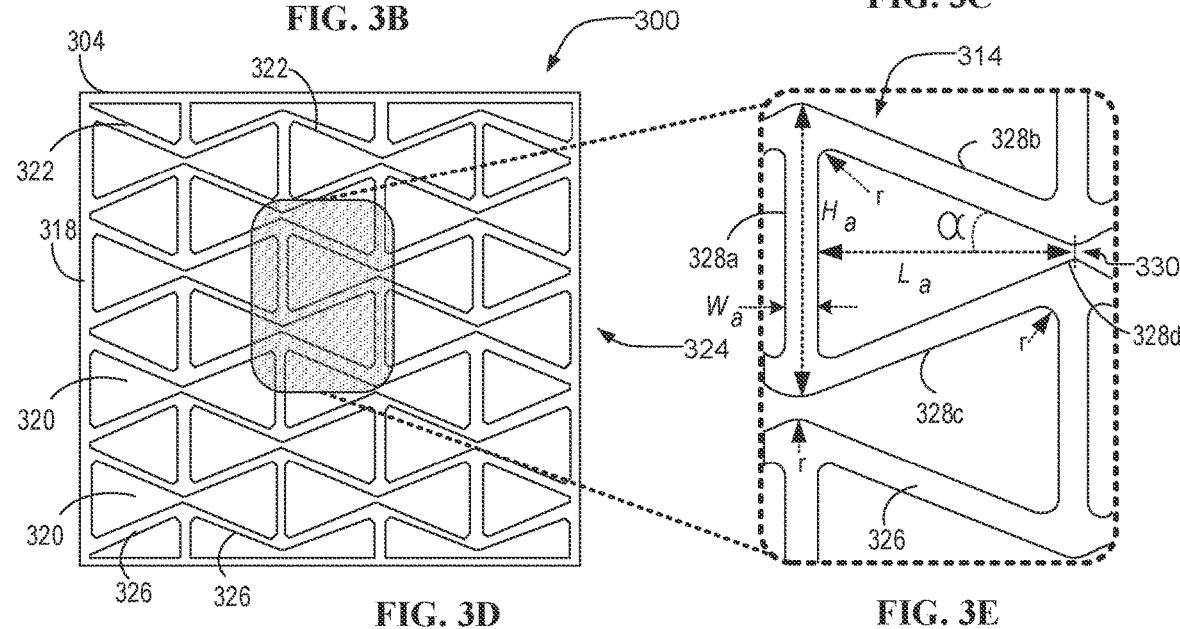
FIG. 3D
FIG. 3E

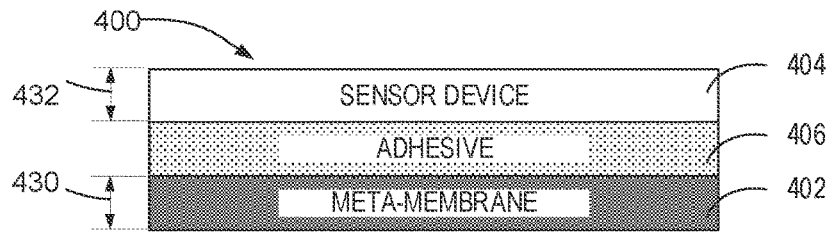
FIG. 4A
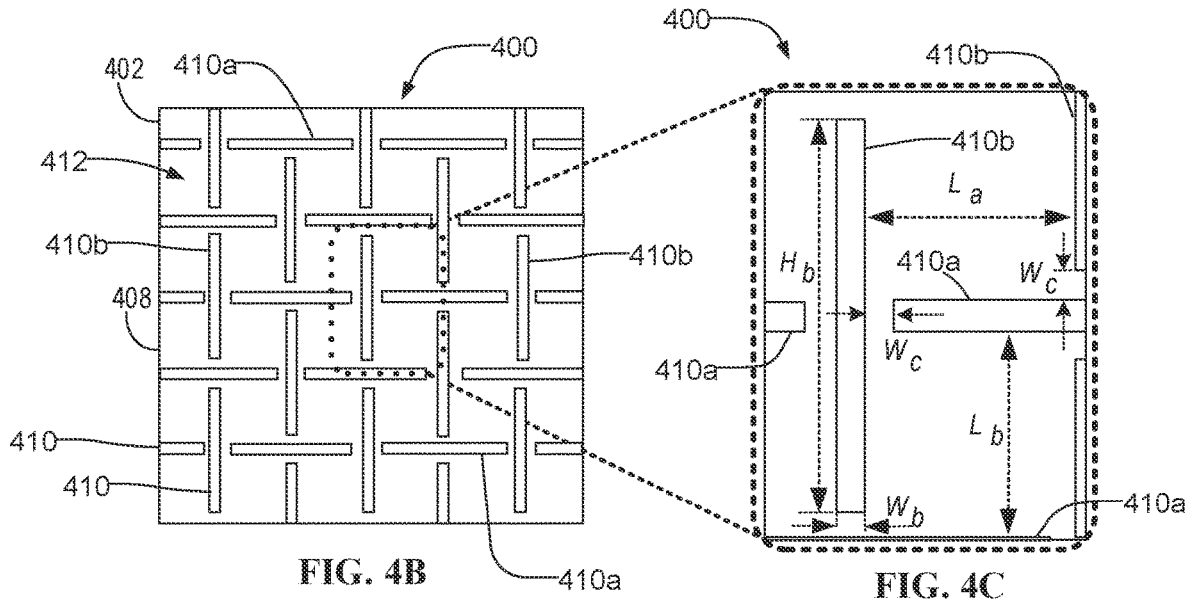
FIG. 4B
FIG. 4C
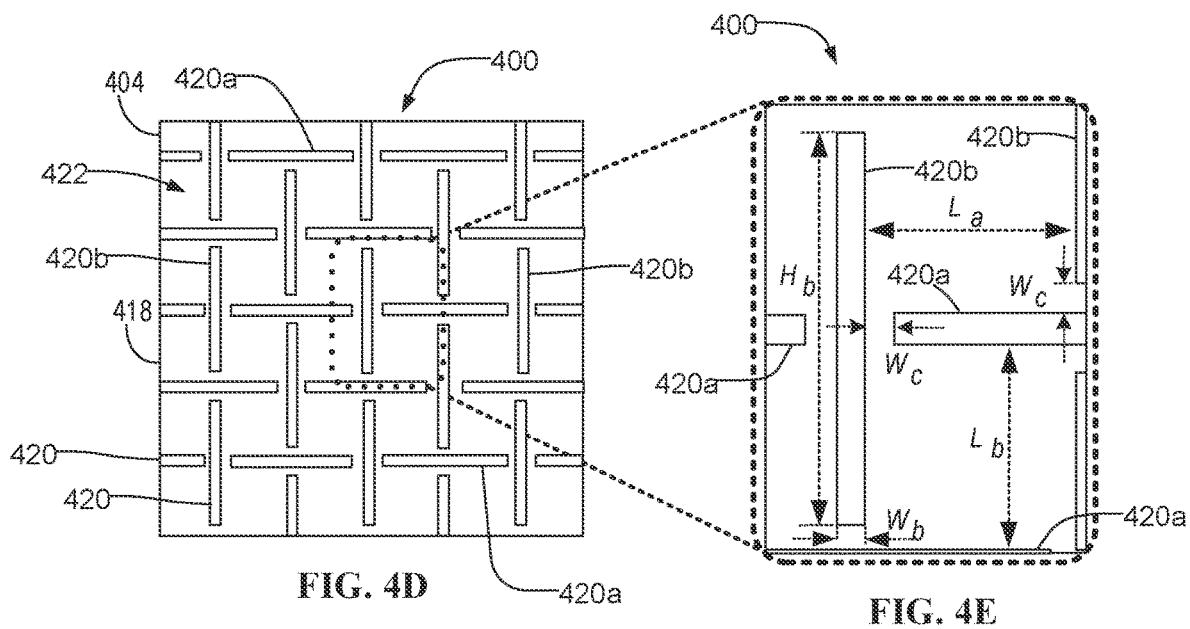
FIG. 4D
FIG. 4E

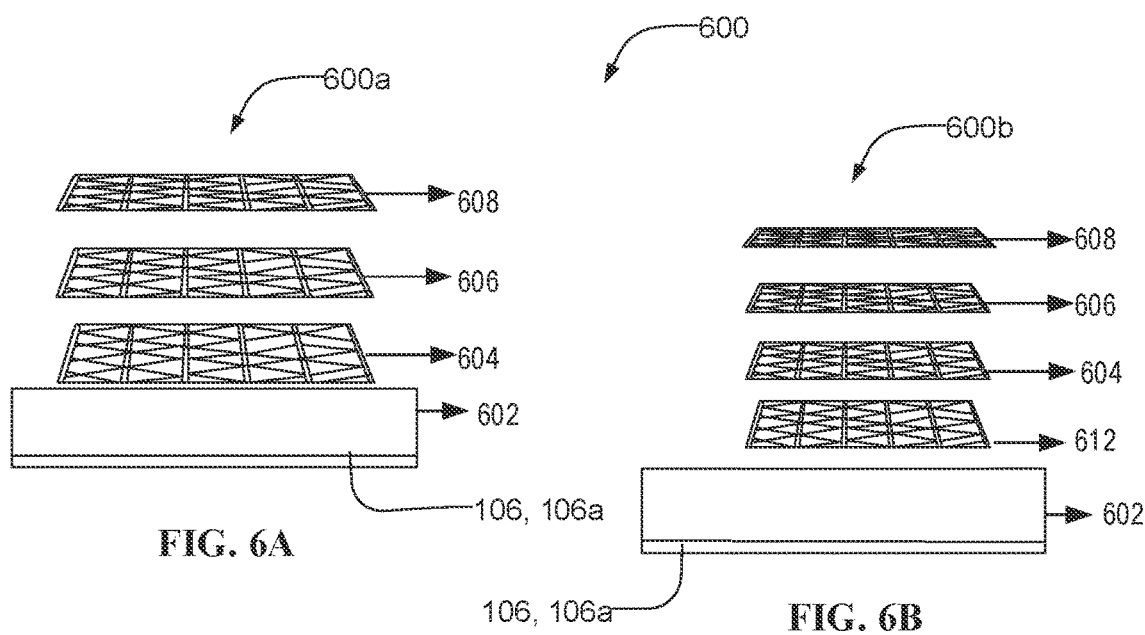
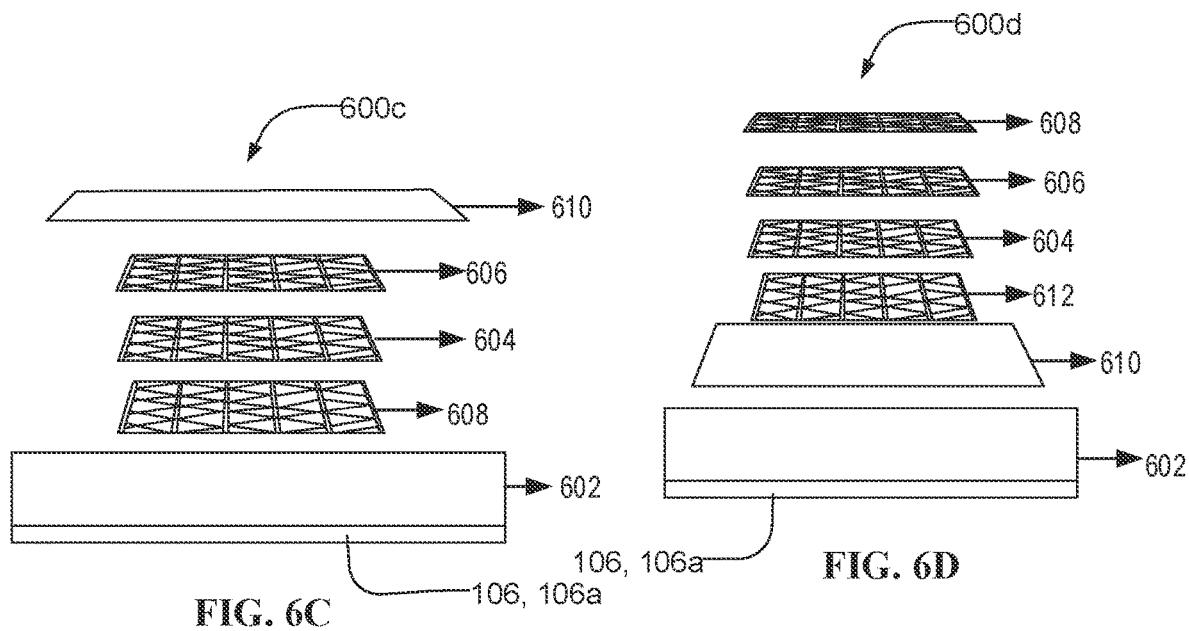

| | POSITION 1 | POSITION 2 | POSITION 3 |
|---|---|---|---|
| SHOULDER CALIBRATION | MOVE ARMS FORWARD AND BACKWARD  1202 | RAISE ARMS UPWARD AND DOWNWARD  1204 | ROTATE/TWIST ARMS (IN CIRCLES)  1206 |
| ELBOW CALIBRATION | CURL/BICEP MOTION — SIDE-EXTENDED ARM 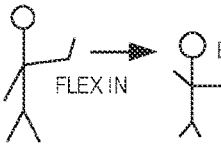 1208 | BEND ELBOW UPWARD/DOWNWARD 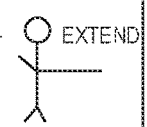 1210 | ROTATEE/TWIST ARMS WITH BENT ELBOW 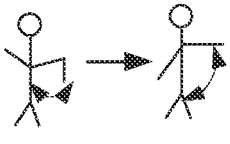 1212 |
| WRIST CALIBRATION | BEND WRIST UPWARD/DOWNWARD 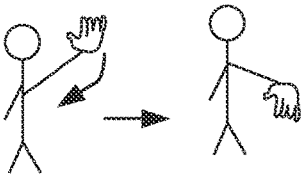 1214 | BEND WRIST LEFT/RIGHT 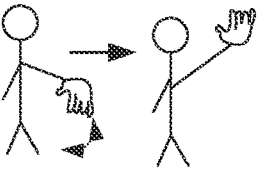 1216 | TWIST WRIST ABOUT FOREARM  1218 |

FIG. 12

ERGONOMICS IMPROVEMENT SYSTEMS HAVING WEARABLE SENSORS AND RELATED METHODS

FIELD OF THE DISCLOSURE

This disclosure relates generally to wearable sensors, and more particularly, to ergonomics improvement systems having wearable sensors and related methods.

BACKGROUND

Warehouse and manufacturing users perform various physical and/or repetitive tasks. Such physical tasks can include lifting and/or holding relatively heavy objects for an extended period of time and/or operations that require numerous repetitive motions (e.g., manually sanding a structure by moving a sanding tool in a circular direction a repeated number of times). Performing a physical task can sometimes result in high strain activity.

SUMMARY

An example ergonomics improvement system disclosed herein includes a wearable ergonomics improvement system. The example ergonomics improvement system includes a membrane having a first frame that includes a plurality of first cutouts defining a first pattern. The system includes a sensor coupled to the membrane that has a second frame having a plurality of second cutouts defining a second pattern, where the first pattern is complementary to the second pattern.

Another example system disclosed herein to track movement of a limb of a body includes a first membrane sensor to couple to a shoulder of the body. The first membrane sensor is to generate outputs in response to movement of a shoulder to detect at least one of a position or rotation of the shoulder. The system includes a second membrane sensor to couple to an elbow of the body to generate second outputs in response to movement of the elbow to detect at least one of a position or rotation of the elbow. The system further incudes a third membrane sensor to couple to a wrist of the body to generate third outputs in response to movement of the hand to detect at least on or a position or rotation of the hand.

An example method disclosed herein includes tracking movement of a limb of a body. The system includes determining a position of the limb relative to the body based on first outputs of a first membrane sensor, second outputs of the second membrane sensor, and third outputs of the third membrane sensor. The system includes determining a position of the limb relative to the body based on first, second, or third outputs received. The system includes receiving a second output from a load sensor carried by the body. The system includes determining a load of the body based on the received second output. The system includes receiving third outputs from a step scanner carried by the body. The system includes determining a foot position by detecting a position of a left foot of the body relative to a position of a right foot of the body based on the third outputs from a pressure sensor. They system includes comparing the determined position of the limb and a position threshold associated with the determined load and the determined foot position. The system includes determining if the determined position exceeds the position threshold. The system includes generating a warning signal if the determined position exceeds the position threshold.

BRIEF DESCRIPTION OF THE DRAWINGS

FIG. 3A is a side view of a portion of an example membrane sensor disclosed herein that can be used to implement the example upper body sensor of FIGS. 1 and 2A.

FIG. 3B is a top view of an example membrane of the example membrane sensor of FIG. 3A.

FIG. 3C is an enlarged portion of the example membrane of FIG. 3B.

FIG. 3D is a top view of an example sensor of the example membrane sensor of FIG. 3A.

FIG. 3E is an enlarged portion of the example sensor of FIG. 3D.

FIG. 4A is a side view of a portion of another example membrane sensor disclosed herein that can be used to implement the example upper body sensor of FIGS. 1 and 2A.

FIG. 4B is a top view of an example membrane of the example membrane sensor of FIG. 4A.

FIG. 4C is an enlarged portion of the example membrane of FIG. 4B.

FIG. 4D is a top view of an example sensor of the example membrane sensor of FIG. 4A.

FIG. 4E is an enlarged portion of the example sensor of FIG. 4D.

FIGS. 6A-6D illustrate other example membrane sensors 600a-d disclosed herein that can be used to implement the example upper body sensor of the example ergonomics improvement system of FIGS. 1 and 2.

FIG. 12 is an example diagram representative of example sensor calibration positions disclosed herein that can be used to implement the example calibration of FIG. 11.

Figure 1:
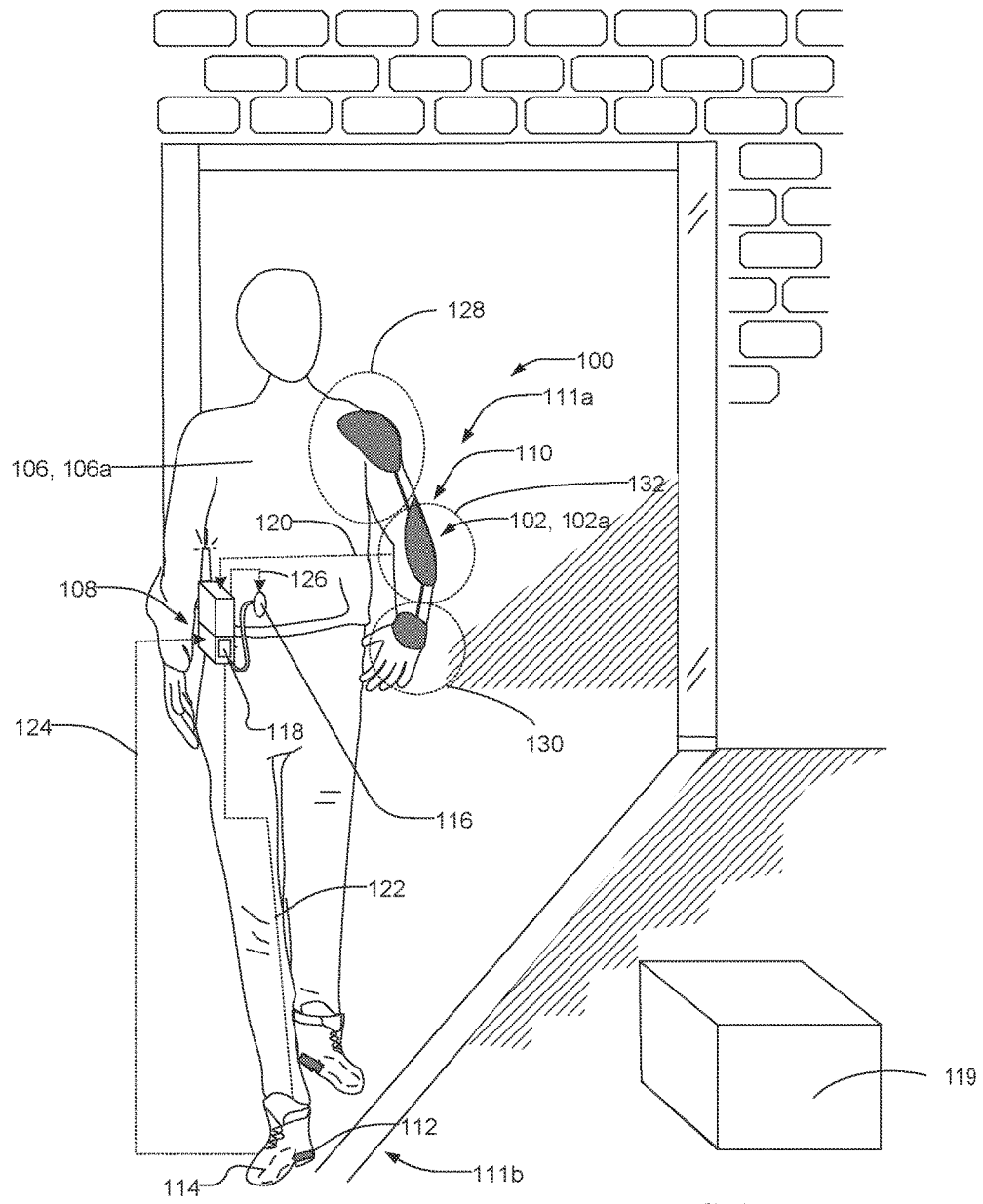
FIG. 1 is an example ergonomics improvement system in accordance with teachings disclosed herein.

The figures are not to scale. Instead, the thickness of the layers or regions may be enlarged in the drawings. In general, the same reference numbers will be used throughout the drawing(s) and accompanying written description to refer to the same or like parts. As used in this patent, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Stating that any part is in "contact" with another part means that there is no intermediate part between the two parts. Although the figures show layers and regions with clean lines and boundaries, some or all of these lines and/or boundaries may be idealized. In reality, the boundaries and/or lines may be unobservable, blended, and/or irregular.

Descriptors "first," "second," "third," etc. are used herein when identifying multiple elements or components which may be referred to separately. Unless otherwise specified or understood based on their context of use, such descriptors are not intended to impute any meaning of priority, physical order or arrangement in a list, or ordering in time but are merely used as labels for referring to multiple elements or components separately for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for ease of referencing multiple elements or components.

DETAILED DESCRIPTION

Manufacturing operations often necessitate users to perform various types of repetitive physical tasks and/or lift objects that are relatively heavy. Performing repetitive physical tasks during certain manufacturing operations can cause undesired risk to users performing such repetitive physical tasks. For example, performing physical tasks repetitively can result in muscle and/or tendon fatigue over time. Muscle fatigue can reduce a strength of a muscle and/or tendon fatigue can reduce structural capacity of a tendon.

To improve ergonomic awareness, ergonomics improvement systems have been developed to monitor and/or quantify musculoskeletal performance during repeated performance of a physical task or manufacturing operation. Generally, existing technologies are focused on gathering posture and/or movement information for treating injuries. For instance, some known systems monitor musculoskeletal performance using sensors to capture data during a repetitive motion. One known system simulation of a person performing the physical tasks over a number of cycles is run by a computer system using the musculoskeletal model for the person and at least one of the task performance data and task description data. The computer simulated model can be used to track motion and/or analyze the detected motion. To capture data for use with a simulated model, some known ergonomics improvement systems employ one or more sensors. The sensors can sense force and/or motion. However, the sensors of these known ergonomics improvement systems do not detect or sense stress and/or strain applied to one or more joints (e.g., a shoulder joint, an elbow joint, a wrist joint, etc.) of an user performing physical tasks.

Example ergonomics improvement systems disclosed herein employ movement, load measurement and/or feet positioning to determine stress and/or strain that a limb, a joint of a limb, and/or a body is undergoing when an user is performing one or more tasks (e.g., physical tasks involving repetitive motion). To track movement of a limb and/or detect stress and/or strain that a joint of a limb is undergoing when a user performs repetitive physical tasks, example ergonomics improvement systems disclosed herein employ one or more wearable sensors. Example wearable sensors disclosed herein, in combination with the ergonomics improvement system, provide a tracking system to track movement of a limb. In some examples, wearable sensors disclosed herein can include example upper body sensor systems, lower body sensor systems, and/or a combination of upper and lower body sensor systems. Data from example wearable sensors disclosed herein (e.g., upper body sensor systems and/or example lower body sensor systems) can be used (e.g., in aggregate or in isolation) to measure one or more of a position of a limb relative to a body, movement of an entire limb relative to a body, stress and/or strain that a joint of a limb is undergoing and/or any other movement(s) or angle(s) of a limb, body portion (e.g., upper back, lower back, etc.) and/or joint relative to a body.

Example wearable sensors disclosed herein include wearable sensors formed from one or more membranes (e.g., a meta-membrane(s)). The membrane(s) can be one or more appliques or patches that can be attached to garments, can be formed as a garment (e.g., a shirt), and/or be a part of garments (e.g., sleeve, etc.). In some examples, wearable sensors disclosed herein include example membrane(s) having Kirigami patterns. In some examples, wearable sensors disclosed herein include example membrane(s) having Auxetic patterns. Kirigami patterns and/or Auxetic patterns provide varying (e.g., increased) flexibility to enable the sensors to accommodate a larger range of motion (e.g., compared to other patterns and/or sensors having a solid surface without patterns). In some examples, the Kirigami and/or Auxetic patterns can be more durable and/or resistant to cracking over time. However, the technical advantages are not limited to these examples. In some examples, wearable sensors disclosed herein can include any other type of meta-membrane(s) and/or membranes having other patterns. For instance, ergonomics improvement systems disclosed herein can employ different types of wearable sensors and/or meta-membrane(s) (e.g., Kirigami, bi-axial Kirigami, Auxetic hexagonal, etc.) that can output signals that can be used to track limb movement, stress, strain, and/or obtain limb position data. In some examples, example wearable sensors disclosed herein can couple (e.g., be attached) to one or more limbs of a body and/or can be positioned across one or more joints to measure stress and/or strain imparted to a limb of a body. For example, the wearable sensors disclosed herein can be attached to an arm of a user to detect stress on a shoulder, elbow and/or a wrist of a user. In some examples, the wearable sensors can be attached to a leg, a hip, a knee, an upper back, and/or a lower back of a user to detect stress and/or strain at a knee, hip, neck, upper back, and/or lower back, etc. In some examples, the wearable sensors can be employed or coupled proximate each joint of a limb to measure or detect a position and/or joint angle of a joint (e.g., a shoulder joint, a wrist joint, etc.) associated with the wearable sensors.

To measure a load carried by a user and detect feet positioning of a user, example ergonomics improvement systems disclosed herein employ the lower body sensor system. To measure load, example lower body sensor systems disclosed herein can employ load cell, a pressure sensor, and/or any other sensor(s) for measuring load and/or weight. To detect feet positioning during physical tasks, example lower body sensor systems disclosed herein can employ Lidar sensors, pressure pads and/or pressure scan sensors, and/or any other suitable positioning sensor(s). Example lower body sensor systems disclosed herein can be carried and/or housed by footwear (e.g., shoes, work boots, etc.) to be worn by a user performing physical tasks. In some examples, example lower body sensors disclosed herein can be placed on and/or within the sole of the footwear. Data from example lower body sensors disclosed herein can be used in aggregate with data collected from example upper body sensor systems disclosed herein to determine movement and/or a position of a limb. However, in some examples, ergonomics improvement systems disclosed herein can employ example upper body sensor systems disclosed herein without example lower body sensor systems disclosed herein to detect a position of a limb relative to a body and/or a joint angle of a joint.

Figure 8A:
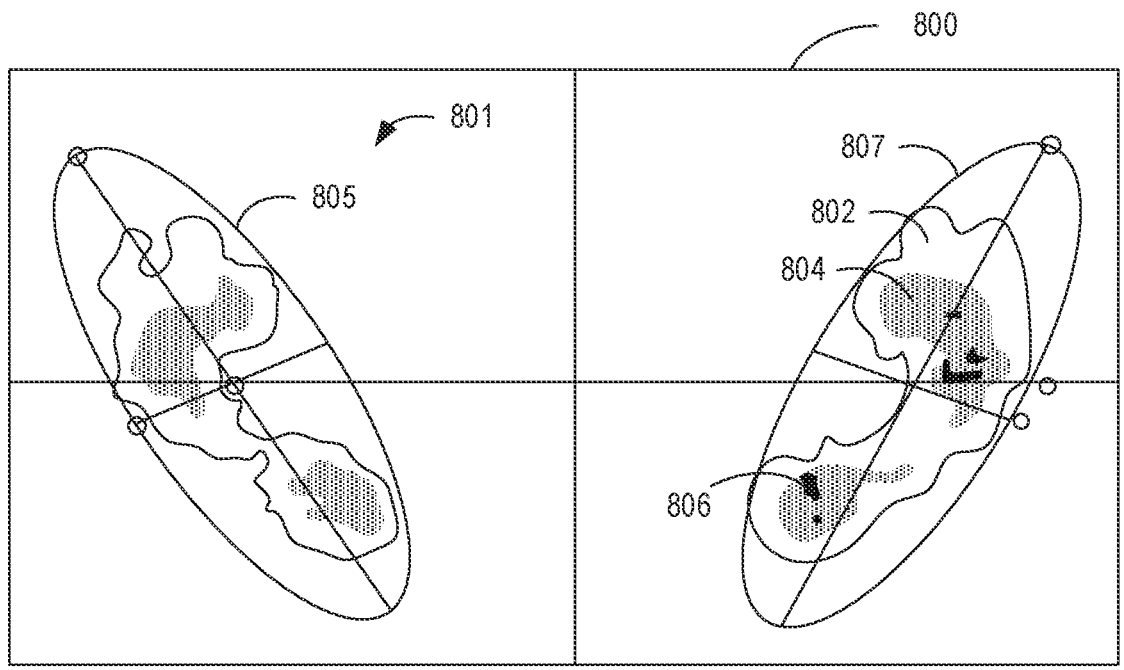
FIGS. 8A and 8B are schematic illustrations of example outputs of the example lower body sensor system of FIG. 7A.

To process data from example wearable sensors disclosed herein (e.g., example upper body and lower body sensor systems), example ergonomics improvement systems disclosed herein employ a controller. In operation, for example, an example controller disclosed herein can receive outputs from the wearable sensors. In some examples, an example controller disclosed herein can compare data from example wearable sensors to a user baseline threshold. For example, the baseline can be pre-determined values based on a first condition and a second condition of the user. For example, the first condition can be an amount of load carried by the person and the second condition can be a stance position of a user's feet when detected carrying the load. For example, a baseline threshold for a person carrying a fifty pound weight while standing in a brace position (e.g., the user's feet are in a brace position as shown in FIG. 8A) will not exceed the baseline threshold. However, the baseline threshold can be exceeded in response to detecting that the user is carrying a fifty pound weight while the user's feet are in a non-brace position (e.g., see FIG. 8B). In some examples, in response to determining that the data of the wearable sensors exceeds the user baseline threshold, example controllers disclosed herein can activate an alarm. Example alarms disclosed herein include, but are not limited to, visual alarms (e.g., a light), audio alarms (e.g., a speaker), haptic feedback (e.g., a vibration), a combination thereof and/or any other alarm(s). In some examples, the type of alarm(s) can be selected based on an environment (e.g., industrial or manufacturing environment) of the user. For example, where the environment can be noisy, busy, or where the tasks being performed should not be interrupted by abrupt or startling alarms, the type of alarm chosen (e.g., haptic feedback) can vary between the options discussed above and/or other types of alarms.

In some examples, example controllers disclosed herein compile outputs from the wearable sensors and transmit the data to a central processing system remotely located from the controller and/or the user. In some such examples, the example central processing system aggregates the data received from the controller and compares the data to a user baseline threshold. In response to determining that the data from the wearable sensors exceeds the user baseline threshold, the example central processing system instructs (e.g., sends a warning signal to) the controller to initiate the example alarm. To provide power to the controller and/or the wearable devices, the example ergonomics improvement system disclosed herein employs a power source. In some examples, an example power source can include a battery. In some examples, an example power source can include smart cloths and/or other devices that generate electricity. As used herein, the term "smart cloths" can include motion-powered fabric(s), fabrics that include integrated circuits that can generate power from sweat and/or friction (e.g., movement), frictional forms of human bio-energy, and/or any other fabric or device for generating energy to power one or more of the wearable devices and/or a controller (e.g., fabric piezoelectric nanogenerators that harvest human mechanical motion to energy).

Examples ergonomics improvement systems disclosed herein can track movement of an upper body (e.g., a shoulder, an elbow, a wrist/hand, a forearm, a lower back, etc.) and/or movement of a lower body (e.g., a hip, a knee, a foot, etc.). For example, to track a movement of a leg, one or more example wearable sensors (e.g., meta-membrane(s)) can be attached to (e.g., skin, clothing) a hip joint, a knee joint, an ankle joint, a lower back, an ankle joint, etc. In some examples, ergonomics improvement systems disclosed herein can track movement of a leg, an arm, a leg and an arm, both arms, both legs, both arms and both legs, an upper back, a lower back, and/or any other limb or portions of a body (e.g., a neck, a lower back, an upper back, etc.) to determine stress and/or strain that a body undergoes when a user performs physical tasks and/or activities.

FIG. 1 is an example ergonomics improvement system 100 in accordance with teachings disclosed herein. The ergonomics improvement system 100 of the illustrated example can detect strain and/or stress that a body undergoes when performing specific work tasks that include repetitive physical tasks. To detect strain and/or stress to a body (e.g., or a joint of a body), the ergonomics improvement system 100 of the illustrated example tracks and/or otherwise detects movement of a limb 102 (e.g., an arm 102a) and/or a joint (e.g., a joint angle, a shoulder joint 128, a wrist joint 130, an elbow joint 132) of the limb 102 relative to a body 106 (e.g., a torso of a body).

The ergonomics improvement system 100 of the illustrated example includes an example controller 108, an example limb sensor 110, an example load sensor 112, an example position sensor 114, an example warning device 116, and an example power device 118. The limb sensor 110, the load sensor 112, the position sensor 114, and the warning device 116 are communicatively coupled to the controller 108 via, for example, a bus, a physical wire, wireless communication protocol, Bluetooth and/or any other suitable communication protocol(s).

To track and/or detect movement of the limb 102 and/or the joint, the ergonomics improvement system 100 of the illustrated example employs the limb sensor 110 (e.g., a tracking system or an upper body sensor). The limb sensor 110 of FIG. 1 is a tracking system that can be coupled (e.g., directly attached) to the limb 102 and/or the joint of the body 106 and/or attached to clothing of the user 106a to obtain data associated with movement of the limb 102 and/or the joint when a user is performing one or more physical tasks (e.g., physical tasks involving repetitive motion). The ergonomics improvement system 100 includes the limb sensor 110, also called a meta-membrane system or sensor, to couple to the limb 102 of the body 106, and generates first outputs in response to movement of the limb 102 relative to the body 106 that are used to determine a position (e.g., an angular and/or rotational position) of the limb 102 relative to the body 106. In the illustrated example, the limb sensor 110 is an upper body sensor system 111a that is attached to the arm 102a of the body 106. However, in other examples, the limb sensor 110 can couple to a leg, a shoulder joint 128, a wrist joint 130, an elbow joint 132, a knee joint, a hip joint, a lower back and/or any other portion of the body 106. For example, the limb sensor 110 can be coupled or attached to the arm 102a, a leg, a hip, a knee neck, a lower back portion, an upper back portion and/or any combination thereof to track movement of one or more limbs and/or joints of a body 106 when the user 106a is performing physical activity. In some examples, multiple limb sensors 110 (e.g., tracking systems, upper body sensors, etc.) can be used to detect movement of multiple limbs or joints of the body 106 when the user 106a is performing a physical activity.

To detect and/or measure a load of the body 106, the ergonomics improvement system 100 of the illustrated example includes the load sensor 112. The load sensor 112 is to generate a second output representative of a load carried by the body 106. The load sensor 112 of FIG. 1 can be a load cell, a pressure sensor, a pressure pad and/or any other sensor(s) for measuring load and/or weight of the body 106.

To detect and/or otherwise determine a stance (e.g., feet positioning) of the user 106a performing a physical task, the ergonomics improvement system 100 of FIG. 1 employs the position sensor 114. The position sensor 114 is to generate a third output representative of a position of a right foot of the body relative to a position of a left foot of the body. The position sensor 114 of FIG. 1 can detect and/or otherwise determine if a user is standing in a stable or bracing position (e.g., with one foot spaced apart and in front of their other foot) or a non-stable or non-bracing position (e.g., the user 106a standing with their feet spaced apart, but the left foot substantially in-line with the right foot) when performing the physical task(s). In some examples, by determining the position of each foot of the user 106a via the position sensor 114, the ergonomics improvement system 100 of FIG. 1 can determine if the user's stance is stable or optimal for carrying a detected load (e.g., an object 119 (e.g., a box)). The load sensor 112 and the position sensor 114 of the illustrated example provide a lower body sensor system 111b of the ergonomics improvement system 100.

To determine stress and/or strain that the limb 102 (e.g., a human limb), the joint, and/or the body 106 (e.g., an upper back, a lower back, etc.) undergoes during a physical task, the ergonomics improvement system 100 includes the controller 108. The controller 108 of FIG. 1 is configured to determine whether one or more physical tasks or actions performed by the user 106a if performed with a less desirable or improper motion based on one or more limb sensor outputs 120, load sensor outputs 122, and/or position sensor outputs 124 received by the controller 108.

To warn the user 106a when the controller 108 determines that detected improper or less desirable movement (e.g., non-ergonomic movement) of the user 106a, the ergonomics improvement system 100 of the illustrated example employs the warning device 116. Based on the data provided by the limb sensor 110, the load sensor 112 and/or the position sensor 114 to the controller 108, the controller 108 controls an operation of the warning device 116 (e.g., via a warning signal 126). The warning device 116 of the illustrated example can include, but is not limited to, a light, an audible alarm, haptic feedback and/or any other alarm(s). The warning device 116 can be carried by the controller 108 (e.g., a housing of the controller 108), a clothing of the user 106a, attached to the body 106, can be carried or integrated with footwear worn by the user 106a, and/or can be carried by a work hat, gloves, and/or any other tool that can be used by the user 106a.

Alternatively, in some examples, the controller 108 of FIG. 1 can be configured to receive the one or more limb sensor outputs 120, the load sensor outputs 122 and/or the position sensor outputs 124 and transmit or communicate the data (e.g., via transmitter) to a remote location (e.g., a remote server, a central processing computer, a control room, etc.). A computer at a remote location can processes the data provided by the limb sensor 110, the load sensor 112, and/or the position sensor 114 to determine if the data represents user activity that exceeds an activity threshold. The remote computer can then communicate (e.g., send) instructions to the controller 108 to activate the warning device 116 if the remote computer determines that the activity exceeds a threshold.

To provide power to the controller 108 and/or the wearable devices or sensors, the example ergonomics improvement system 100 disclosed herein employs the power device 118 (e.g., a power source). The power device 118 of FIG. 1 provides power to the controller 108, the limb sensor 110, the load sensor 112, the position sensor 114, and/or the warning device 116. In some examples, the power device 118 provides power only to the controller 108 and/or the warning device 116. For example, the controller 108, the power device 118, the limb sensor 110, the load sensor 112, the position sensor 114 and the warning device 116 can be electrically coupled via one or more electrical wires. In some examples, the limb sensor 110, the load sensor 112, and the position sensor 114 are powered with dedicated power devices (e.g., batteries) independent from the power device 118 and/or the controller 108. In some examples, the limb sensor 110, the load sensor 112, and/or the position sensor 114 are powered indirectly by the power device 118 through connection(s) with the controller 108. For example, the power device 118 (e.g., a battery) can be electrically coupled with (e.g., to provide power to) the limb sensor 110, the load sensor 112, the position sensor 114, the controller 108 and/or the warning device 116. In some examples, the limb sensor 110, the load sensor 112 and the position sensor 114 have dedicated batteries and do not require power from the power device 118.

The power device 118 of the illustrated example is a battery. In some examples, the power device 118 can include smart cloths and/or other device(s) that generate electricity. As used herein, the term "smart cloths" can include motion-powered fabric(s), fabrics that include integrated circuits that can generate power from sweat and/or frictional movement, frictional forms of human bio-energy, and/or any other fabric or device for generating energy to power the ergonomics improvement system 100 (e.g., one or more of the limb sensor 110, the load sensor 112, the position sensor 114, the warning device 116 and/or a controller 108).

Figure 2A:
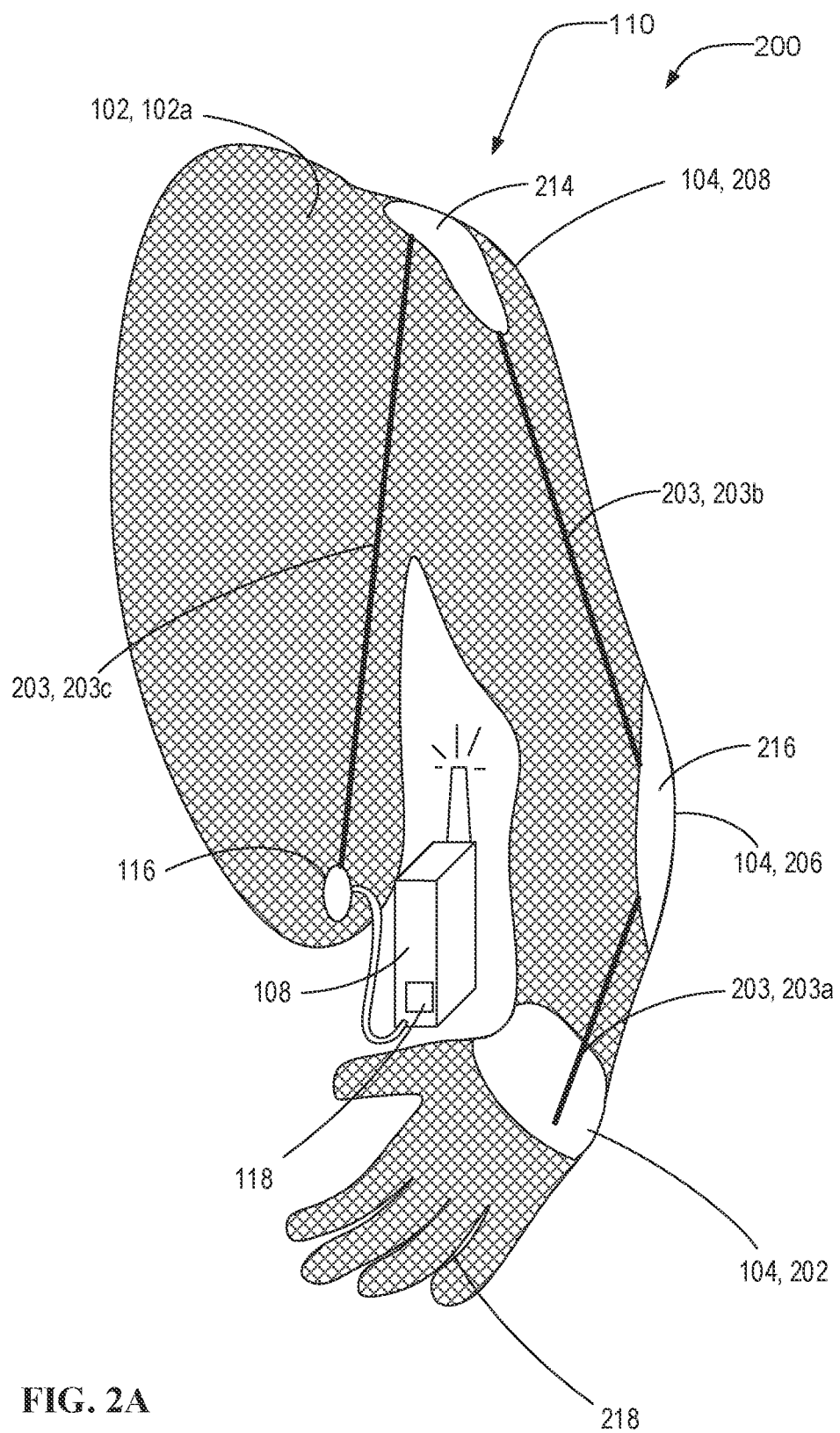
FIG. 2A is an enlarged portion of an example upper body sensor of the example ergonomics improvement system of FIG. 1.

FIG. 2A is a perspective, enlarged view of the limb sensor 110 (e.g., the upper body sensor system 111a) of the example ergonomics improvement system 100 of FIG. 1. The limb sensor 110 of the illustrated example is a wearable membrane that couples (e.g., attaches) to the arm 102a (or limb) of the body 106. In the illustrated example, the limb sensor 110 includes a plurality of membrane sensors 200 that generate first outputs to track movement of the limb 102 or arm 102a.

The membrane sensors 200 of the illustrated example of FIG. 2 include a first membrane sensor 214 (e.g., a first membrane assembly), second membrane sensor 216 (e.g., a second membrane assembly), and a third membrane sensor 218 (e.g., a third membrane assembly). In the illustrated example of FIG. 2, the first membrane sensor 214 (e.g., a shoulder membrane sensor system) is coupled adjacent or proximate a shoulder 208, the second membrane sensor 216 (e.g., an elbow membrane sensor) is coupled adjacent or proximate an elbow 206, and the third membrane sensor 218 (e.g., hand membrane sensor) is coupled adjacent or proximate a wrist 202.

Each of the membrane sensors 200 detects movement of the user 106a and obtains (e.g., measure or calculate) movement data. For example, the limb sensor 110 of FIG. 2 includes the first membrane sensor 214 positioned proximate the shoulder 208 to generate first ones of first outputs (e.g., the limb sensor outputs 120) in response to movement of the shoulder 208 that can be used to detect a position of the shoulder 208 relative to the body 106. For example, the limb sensor 110 of FIG. 2 includes the second membrane sensor 216 positioned proximate the elbow 206 to generate first ones of second outputs (e.g., the limb sensor outputs 120) in response to movement of the elbow 206 that can be used to detect a position of the elbow 206 relative to the body 106. For example, the limb sensor 110 of FIG. 2A includes the third membrane sensor 218 positioned proximate the elbow 206 to generate first ones of third outputs (e.g., the limb sensor outputs 120) in response to movement of the hand/wrist 204 that can be used to detect a position of the hand/wrist 204 relative to the body 106.

Although the limb sensor 110 of FIG. 2A includes the membrane sensors 200, in some examples, the limb sensor 110 can include only one sensor assembly (e.g., the first membrane sensor 214), two membrane sensors, more than three membrane sensors, and/or any other number of membrane sensors 200.

In some examples, the membrane sensors 200 can be implemented on cloth, woven fabric, or other material or apparel that can be worn by the user 106a. Additionally, each of the membrane sensors 200 of the illustrated example are formed as pads or patches that attach to a limb 102 and/or clothing of the user 106a. For example, the membrane sensors 200 can be attached to a sleeve or wearable device that can be removably worn by the user 106a. In some examples, each of the membrane sensors 200 of the illustrated example can include releasable fasteners such as, for example, a hook and loop fastener, Velcro® brand fastener, straps and/or any other releasable fastener that can secure the membrane sensors 200 to the limb 102 of the body 106. In some examples, membrane sensors 200 can be formed as a unitary membrane or wearable device that can be worn by the user 106a. For instance, the membrane sensors 200 can be formed as a sleeve or as shirt (e.g., an entire shirt composed of a membrane sensor) or other clothing that can be worn by the user 106a. In other words, instead of the first membrane sensor 214, the second membrane sensor 216, and the third membrane sensor 218, an example limb sensor 110 can include a shirt that is formed of a unitary membrane sensor. In other words, the entire shirt can be a sensor and/or include sensor functionality. In some examples, the membrane sensor can be formed as a wearable device that can include, but is not limited to, a sleeve, a shirt, an attachable cloth, a sleeve, a rubber or flexible sleeve and/or any other wearable device or clothing. The membrane sensors 200 can be permanently attached to the cloth or piece of apparel and/or it can be removal and reattachable. In other examples, the membrane sensors 200 are directly attached to the arm 102a of the user 106a via removable adhesive, tape, etc.

To couple (e.g., communicatively and/or electrically) the membrane sensors 200, the controller 108, the warning device 116 and/or the power device 118, the ergonomics improvement system 100 of FIGS. 1 and 2 includes one or more wires 203 (e.g., an electrical wire). For example, the membrane sensors 200, the controller, the warning device 116 and/or the power device are electrically coupled in series. For instance, the third membrane sensor 218 is connected electrically to the second membrane sensor 216 via a first wire 203a, the second membrane sensor 216 is connected electrically to the first membrane sensor 214 via a second wire 203b, and the first membrane sensor 214 is connected electrically to the warning device 116 via a third wire 203c. Alternatively, in some examples, the membrane sensor 200, the controller 108, the warning device 116 and/or the power device 118 can be communicatively coupled via wireless connection, a Bluetooth connection, and/or any other communication protocol. In some examples, the power device 118 provides power to the membrane sensors 200. In some examples, each of the membrane sensors 200 is powered by independent power sources (e.g., batteries, smart cloths, etc.) and include one or more antennas to transmit data (e.g., the limb sensor output 120) to the controller 108. In some examples, the wires 203 can be omitted.

Figure 2B:
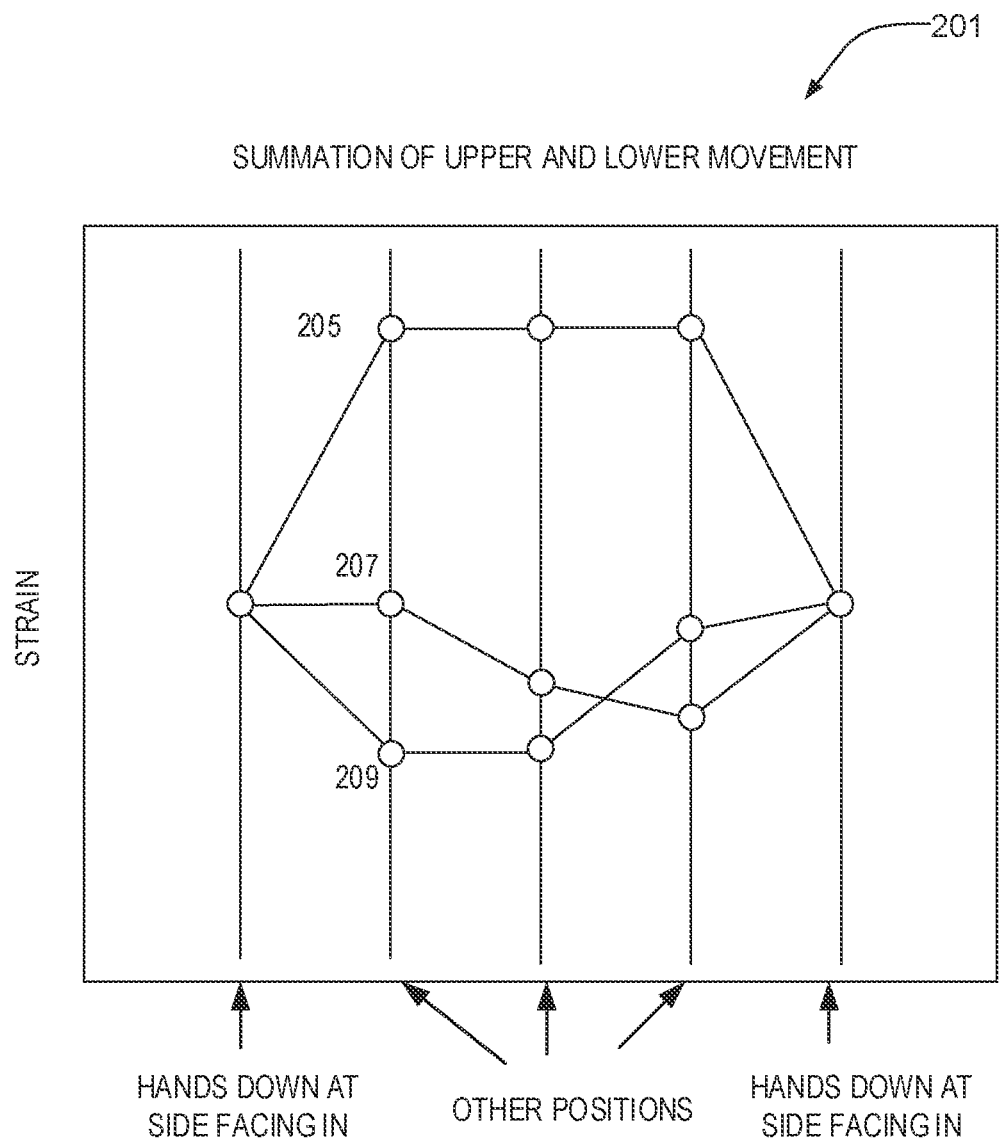
FIG. 2B is a schematic illustration of example outputs of the example upper body sensor of FIG. 2A.

FIG. 2B is an example diagram 201 illustrating example sensor outputs 205-209 of the example membrane sensors 200 (e.g., the first membrane sensor 214, the second membrane sensor 216, the third membrane sensor 218) of FIG. 2. In operation, the first membrane sensor 214 provides first ones of the first sensor outputs (e.g., the limb sensor outputs 120). Specifically, during movement of the shoulder 208, the first membrane sensor 214 generates a first sensor output 205. Based on a position of the elbow 206 (e.g., bent or straight), the second membrane sensor 216 generates a second sensor output 207. Based on a position of the hand (e.g., bent or straight at the wrist) and/or a position of a forearm (e.g., twist position or rotational position relative to a longitudinal axis along the forearm), the third membrane sensor 218 of the illustrated example generates a third sensor outputs 209.

Each example of the sensor outputs 205-209 is representative of movements of the arm 102a relative to an initial position (e.g., the arm 102a positioned against the side of the body 106 with palm against the body 106). The example sensor outputs 205-209 are representative of, and/or can be used to, detect an amount of strain imparted to the arm 102a during movement as the shoulder 208 rotates relative to the body 106, the elbow 206 bends at the elbow joint, the hand bends at the wrist 202, the arm 102a rotates relative to the shoulder 208, the forearm twists relative to the elbow and/or the shoulder, and/or any other position of the arm 102a relative to the body 106. The other positions can include various positions (e.g., rotating the arm 102a outward, lifting the arm 102a above a user's head, rotating the arm 102a in a circle, etc.). The outputs 205-209 can be a voltage signal, a current signal and/or any other type of signal.

FIG. 3A-3E illustrate an example membrane sensor 300 that can implement membrane sensors 200 of the example ergonomics improvement system 100 of FIGS. 1 and 2. The membrane sensor 300 of the illustrated example includes a membrane 302 (e.g., a membrane layer) and a sensor 304 (e.g., a sensor layer). FIG. 3A is a side view of the example membrane sensor 300. FIG. 3B is a top view of the example membrane 302 and FIG. 3C is an enlarged portion of the example membrane 302 of FIG. 3B. FIG. 3D is a top view of the example sensor 304 and FIG. 3E is an enlarged portion of the example sensor 304 of FIG. 3D. For example, the membrane sensor 300 of the illustrated example can implement the first membrane sensor 214, the second membrane sensor 216 and/or the third membrane sensor 218 of FIG. 2. The membrane sensor 300 of FIGS. 3A-3E can be formed or shaped to similar to the first membrane sensor 214, the second membrane sensor 216, the third membrane sensor 218, and/or can have any other shape (e.g., a waist band, a belt, etc.) to fit on and/or around a portion of the body 106. Additionally, the membrane sensor 300 of the illustrated example is flexible and can conform (e.g., bend, wrap, etc.) to portions (e.g., the shoulder 208, the elbow 206, the wrist 202 of FIG. 2) of the body 106.

Referring to FIGS. 3A-3E, the membrane 302 of the illustrated example couples to the sensor 304 via adhesive 306 (e.g., an adhesive layer 306). In the illustrated example, the adhesive 306 is positioned between the membrane 302 and the sensor 304. The adhesive 306 can include, but is not limited to, a plastic, a tape, glue, a paste, and/or any other type of adhesive. The membrane 302 of the illustrated is a hexagonal meta-membrane. For example, the membrane 302 of FIG. 3B includes a first frame 308. To improve or increase flexibility characteristics of the membrane sensor 300, the first frame 308 includes a plurality of first openings or cutouts 310. As a result, the frame 308 includes a plurality of flexible legs 312 (e.g., strips, frame portions, etc.) that are formed by the first cutouts 310. The first frame 308 (e.g., via the first legs 312 and/or the first cutouts 310) defines a first pattern 314 (e.g., an auxetic hexagonal pattern). In particular, the first pattern 314 is an Auxetic or hexagonal pattern. The membrane 302 can be rubber, plastic, aluminum, copper, and/or any other material(s) that can flex or conform to a part of the body 106.

Referring to FIG. 3D, the sensor 304 is an electrical sensor (e.g., a strain sensor) that generates electrical outputs based on a flexed position of the sensor 304. For example, the sensor 304 of FIGS. 3A-3E can be a strain sensor, piezoelectric sensor, a flex circuit and/or any other flexible sensor that provides and/or generates output signals (e.g., the limb sensor outputs 120) when flexed, bent, and/or otherwise moved relative to an initial position. For example, the electrical signals output by the sensor 304 can be communicated to the controller 108 via the wires 203 (FIG. 2).

The sensor 304 of the illustrated example includes a second frame 318. To improve or increase flexibility and/or stretchability characteristics of the membrane sensor 300, the second frame 318 includes a plurality of second openings or cutouts 320. As a result, the second frame 318 includes a plurality of flexible second legs 322 (e.g., strips, frame portions, etc.) that are formed by the second cutouts 320. The second frame 318 (e.g., via the second legs 322 and/or the second cutouts 320) defines a second pattern 324 (e.g., auxetic hexagonal pattern). In particular, the second pattern 324 is an Auxetic. In the illustrated example, the first pattern 314 of the membrane 302 is complementary (e.g., identical) to the second pattern 324. For example, FIGS. 3C and 3E are enlarged views of the membrane 302 of FIG. 3B and the sensor 304 of FIG. 3D, respectively. Referring to FIGS. 3C and 3E, each of the first pattern 314 and the second pattern 324 includes substantially similar (e.g., identical) dimensional characteristics. As used herein, "substantially similar identical dimensional characteristics" means that dimensions of the membrane 302 and the sensor 304 are identical or within a certain manufacturing tolerance (e.g., between approximately 0.5 percent and 10 percent). The first pattern 314 and the second pattern 324 include a plurality of interconnected triangular-shaped portions or sections 326 that each include a dimensional length La, a dimensional height Ha, an angle α, a thickness Wa, and radii r as shown in FIGS. 3C and 3E. For example, the dimensional height $H_a$ is a length of a base 328a of a triangular section 326a. The angle α symbol is an of respective side legs 328b, 328c of the triangular section 326a relative to horizontal. The dimension $L_a$ is a distance between a tip 328d of the triangular section 326a and the base 328a of the triangular section 326a. The tip 328d is defined by respective ends of the legs 328b, 328c opposite the base 328a. The respective ends of the legs 328b, 328c proximate the tip 328d are not connected (e.g., are disconnected) to form a gap 329 therebetween. The radius r is a radius of corners of the triangular-shaped sections 326. The dimension Wa is a width of the legs 312, 322 of the respective first and second patterns 314, 324. The dashed lines in FIGS. 3C and 3E are part of dimension lines and form no part of the first pattern 314 and the second pattern 324. Additionally, the first cutouts 308 extend (e.g., completely) through a meta-membrane thickness 330 (FIG. 3A) of the membrane 302 and the second cutouts 320 extend (e.g., completely) through a sensor device thickness 332 (e.g., FIG. 3A) of the sensor 304. However, in some examples, the first cutouts 308 and/or the second cutouts 320 can be formed as recessed cavities that do not extend (e.g., completely) through (or partially extend through a portion) the respective meta-membrane thickness 330 and sensor device thickness 332 of the membrane 302 and/or the sensor 304. Table 1 below provides example dimensional values that can be used to implement the first pattern 314 and/or the second pattern 316. The example dimensions are provided as an example and the membrane sensor 300 is not limited to the parameters, values, and units shown. In other examples, the membrane sensor 300 can be formed with any other dimensional values.

TABLE 1

| PARAMETER | VALUE | UNIT |
| --- | --- | --- |
| $W_a$ | 0.25 | millimeter |
| $L_a$ | 2.25 | millimeter |
| $H_a$ | 2.5 | millimeter |
| r | 0.5 | millimeter |
| α | 29 | Degree |

FIGS. 4A-4E illustrate another example membrane sensor 400 disclosed herein that can implement the example ergonomics improvement system 100 of FIGS. 1 and 2. The membrane sensor 400 of the illustrated example includes a membrane 402 (e.g., a membrane layer) and a sensor 404 (e.g., a sensor layer). FIG. 4A is a side view of the example membrane sensor 400. FIG. 4B is a top view of the example membrane 402 and FIG. 4C is an enlarged portion of the example membrane 402 of FIG. 4B. FIG. 4D is a top view of the example sensor 404 and FIG. 4E is an enlarged portion of the example sensor 404 of FIG. 4D. For example, the membrane sensor 400 of the illustrated example can implement the first membrane sensor 214, the second membrane sensor 216 and/or the third membrane sensor 218 of FIG. 2. The membrane sensor 400 of FIGS. 4A-4E can be formed or shaped similar to the first membrane sensor 214, the second membrane sensor 216, the third membrane sensor 218, and/or can have any other shape (e.g., a waist band, a belt, etc.) to fit on and/or around a portion of the body 106. Additionally, the membrane sensor 400 of the illustrated example is flexible and can conform (e.g., bend, wrap, etc.) to portions (e.g., the shoulder 208, the elbow 206, the wrist 202 of the body 106.

Referring to FIGS. 4A-4E, the membrane 402 of the illustrated example couples to the sensor 404 via adhesive 406 (e.g., an adhesive layer). The adhesive 406 can include a plastic, tape, glue, latex strip, and/or any other type of adhesive. In the illustrated example, the adhesive 406 is positioned between the membrane 402 and the sensor 404. The membrane 402 of the illustrated example includes a first frame 408. The first frame 408 of FIGS. 4A and 4E includes a plurality of first openings or cutouts 410 defining a first pattern 412 to improve or increase flexibility and/or stretchability characteristics of the membrane sensor 400. Specifically, the first pattern 412 of the illustrated example is a Kirigami pattern (e.g., a bi-axial Kirigami pattern). The membrane 402 can be rubber, plastic, aluminum, copper, and/or any other material(s) that can flex or conform to a part of the body 106.

Referring to FIG. 4D, the sensor 404 is an electrical sensor (e.g., a strain sensor) that generates electrical outputs based on a flexed position of the sensor 404. For example, the sensor 404 of FIGS. 4A-4E can be a strain sensor, piezoelectric sensor, a flex circuit and/or any other flexible sensor that provides and/or generates output signals (e.g., the limb sensor outputs 120) when flexed, bent, and/or otherwise moved relative to an initial position. For example, the electrical signals output by the sensor 404 can be communicated to the controller 108 via the wires 203 (FIG. 2).

The sensor 404 includes a second frame 418 having a plurality of second openings or cutouts 420 defining a second pattern 422. In particular, the second pattern 422 of the illustrated example is a Kirigami pattern. In other words, the first pattern 412 is complementary (e.g., identical) to the second pattern 422. For example, FIGS. 4C and 4E are enlarged views of the membrane 402 of FIG. 4B and the sensor 404 of FIG. 4D, respectively.

Referring to FIGS. 4C and 4E, each of the first pattern 412 and the second pattern 422 includes substantially similar (e.g., identical) dimensional characteristics. As used herein, "substantially similar identical dimensional characteristics" means that dimensions of the membrane 402 and the sensor 404 are identical or within a certain manufacturing tolerance (e.g., between approximately 0.5 percent and 10 percent). For example, the first cutouts 410 of the first pattern 412 have a first set 410a of the first cutouts 410 positioned in a first orientation and a second set 410b of the first cutouts 410 positioned in a second orientation different than the first orientation. For example, the first set 410a of the first cutouts 410 is substantially perpendicular to the second set 410b of the first cutouts 410. Likewise, for example, the second cutouts 420 of the second pattern 422 have a first set 420a of the second cutouts 420 positioned in a first orientation and a second set 420b of the second cutouts 420 positioned in a second orientation different than the first orientation. For example, the first set 420a of the second cutouts 420 is substantially perpendicular (e.g., perfectly orthogonal or almost perfectly orthogonal (e.g., within 10 degrees of perpendicularity)) to the second set 420b of the second cutouts 420. The first cutouts 410 and the second cutouts 420 each include a length $H_b$ and a width $W_b$. Additionally, a distance Wc separates respective ones of the first set 410a of the first cutouts 410a and respective ones of the second set 410b of the first cutouts 410. Likewise, a distance Wc separates respective ones of the first set 420a of the second cutouts 420, and respective ones of the second set 420b of the second cutouts 420. A length $L_a$ is a distance between respective ones of the first set 410a of the first cutouts 410, and respective ones of the first set 420a of the second cutouts 420. The length $L_b$ is a distance between respective ones of the second set 410b of the first cutouts 410 and respective ones of the second set 420b of the second cutouts 420. In the illustrated example, the width $W_b$ and the distance Wc are equivalent. Likewise, the length $L_a$ and length $L_b$ are equivalent. However, in some examples, the width $W_b$ and the distance Wc and/or the length $L_a$ and length $L_b$ can be different values. Additionally, the first set 410a of the first cutouts 410 can be oriented at an angle relative to the second set 410b of the first cutouts 410 and/or the first set 420a of the second cutouts 420 can be oriented at an angle relative to the second set 420b of the second cutouts 420. In some examples the first cutouts 410 and/or the second cutouts 420 can have any other suitable pattern. Additionally, the first cutouts 410 extend (e.g., completely) through a meta-membrane thickness 430 (FIG. 4A) of the membrane 402 and the second cutouts 420 extend (e.g., completely) through a sensor device thickness 432 (FIG. 4A) of the sensor 404. However, in some examples, the first cutouts 410 and/or the second cutouts 420 can be formed as recessed cavities (e.g., slots, slits, channels, etc.) that do not extend (e.g., completely) through (or partially extend through a portion) the respective meta membrane thickness 430 and sensor device thickness 432 of the membrane 402 and/or the sensor 404. Table 2 below provides example dimensional values that can be used to implement the first pattern 412 and/or the second pattern 422. The example dimensions are provided as an example and the membrane sensor 400 is not limited to the parameters, values, and units shown. In other examples, the membrane sensor 400 can be formed with any other dimensional values.

TABLE 2

| PARAMETER | VALUE | UNIT |
| --- | --- | --- |
| $W_b$ | 0.25 | millimeter |
| $W_C$ | 0.25 | millimeter |
| $L_a$ | 1.75 | millimeter |
| $L_b$ | 1.75 | millimeter |
| $H_b$ | 3.25 | millimeter |

Figure 5:
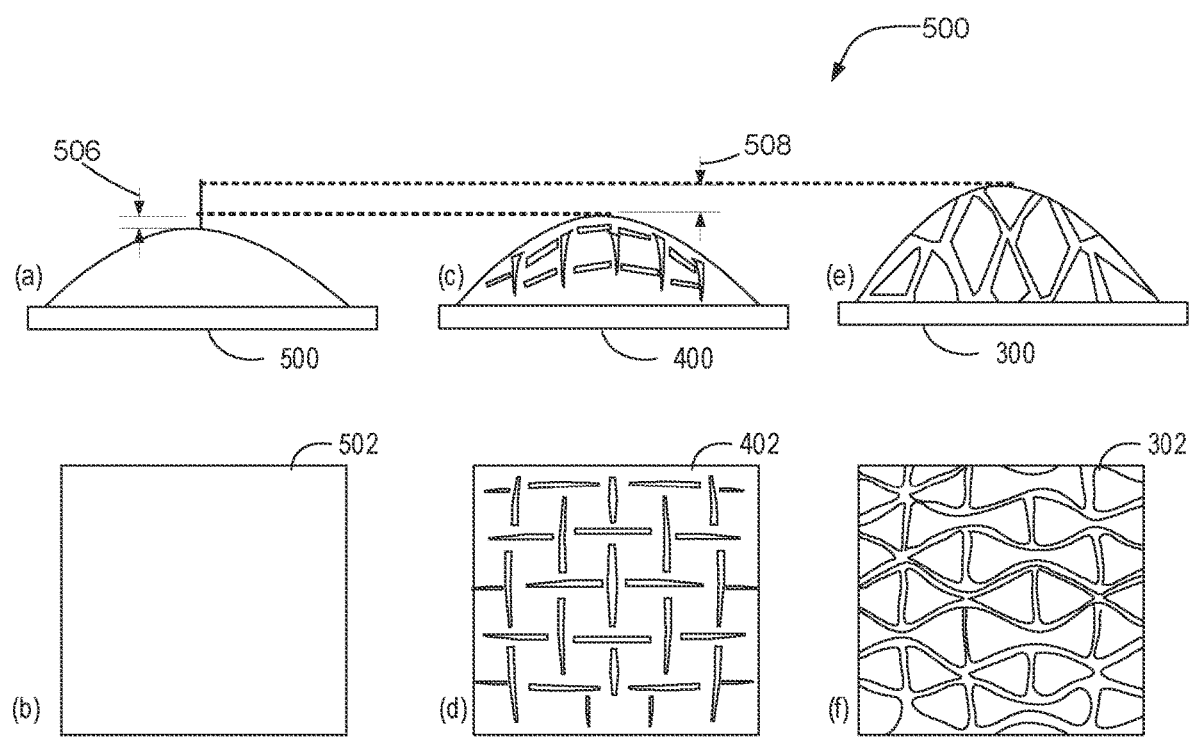
FIG. 5 is a schematic illustration of example displacement and stress distributions of a baseline membrane sensor, the example membrane sensor of FIGS. 3A-3E and the example membrane sensor of FIGS. 4A-4E.

FIG. 5 is a schematic illustration of example displacement and stress distribution of a membrane sensor 500, the example membrane sensor of FIGS. 3A-3E and the example membrane sensor of FIGS. 4A-4E. The membrane sensor 500 includes a membrane 502 that is formed without cutouts or openings. FIG. 5 illustrates side views of the membranes sensor 500, the membrane sensor 400 and the membrane sensor 300 labeled as (a), (c), and (e), respectively. FIG. 5 also illustrates top views of the membranes sensors 500, 400, 300 labeled as (b), (d), and (f), respectively. The membrane sensor 500, the membrane sensor 400 and the membrane sensor 300 are shown in respective flexed or stretched positions when a similar or identical force (or a flex position of the arm 102a) is imparted to the respective membrane sensors 500, 400, 300. FIG. 5 illustrates differences in flexibility between membrane sensors 500, 400, and 300. The membrane sensor 400 can flex greater than the membrane sensor 300 by a height 506 (e.g., approximately between 10% and 20% greater flexibility). The membrane sensor 500 can flex greater than the membrane sensor 400 by a height 508 (e.g., between approximately 10% and 40% greater flexibility than the membrane sensor 400 and/or between approximately 30% and 755 greater flexibility than the membrane sensor 500). Stress-strain mapping is shown in the membrane sensors 500, 400 and 300 when the membrane sensors 500, 400, 300 are flexed to the positions shown in FIG. 5. A strain key 510 to indicate levels of strain. Although the membrane sensor 500 stretches or flexes the least amount, the membrane sensor 500 experiences a greater amount of strain and/or stress compared to the membrane sensors 400 and 500.

FIGS. 6A-6D illustrate other example membrane sensors 600a-d disclosed herein that can be used to implement the ergonomics improvement system of FIGS. 1 and 2. The membrane sensors 600a-d (e.g., strain sensors, flex circuit) can be assembled in various configurations including, for example, including a first membrane sensor 600a, a second membrane sensor 600b, a third membrane sensor 600c, and a fourth membrane sensor 600d. For example, the membrane sensors 600a-600d can implement the example membrane sensors 200 of FIG. 2, the membrane sensors 300 of FIGS. 3A-3E, and/or the membrane sensors 400 of FIG. 4A-4E.

The first membrane sensor 600a includes a membrane 604 (e.g., a wearable membrane), a sensor 608 (e.g., strain sensing element), and a first adhesive 606 (e.g., an adhesive layer) that can couple or attach (e.g., directly) to skin 602 of the user 106a. In the illustrated example, the membrane 604 attaches to the skin 602 of the user 106a. The first adhesive 606 is positioned between the membrane 604 and the sensor 608 and couples or attaches the membrane 604 and the sensor 608. When coupled to the body 106, the membrane 604 is between a first side of the first adhesive 606 and the skin 602 of the user 106a (e.g., above the skin 602), and the sensor 608 is positioned adjacent or proximate (e.g., directly engaged with) a second side of the first adhesive 606 opposite the first side.

The second membrane sensor 600b includes the sensor 608, the first adhesive 606, the membrane 604, and a second adhesive 612. The second adhesive 612 can be used to couple (e.g., directly couple) the membrane 604 to the skin 602 of the user 106a. The membrane 604 is positioned between the first adhesive 606 and the second adhesive 612, and the second adhesive 612 is positioned between the membrane 604 and the skin 602 when coupled to the body 106. The first adhesive is positioned between and couples the membrane 604 and the sensor 608.

The third membrane sensor 600c includes the membrane 604 positioned between the sensor 608 and the first adhesive 606. For example, the sensor 608 attaches to and/or is integrally formed with the membrane 604. The first adhesive 606 couples or attaches the membrane 604 and the sensor 608 to clothing 610 to be worn by the user 106a. When worn by the user 106a, the clothing 610 retains or maintains the membrane sensor 600a on the user 106a. The sensor 608 is positioned proximate (e.g., directly engaged with) the skin 602 of the user 106a when the clothing 610 having the membrane sensor 600c is worn by the user 106a. In other words, the sensor 608 is inside or located on an interior side of the clothing 610 when the clothing 610 is worn by the user 106a.

The fourth membrane sensor 600d includes the sensor 608, the first adhesive 606, the membrane 604, the second adhesive 612 and the clothing 610. The first adhesive 606 couples or attaches the membrane 604 and the sensor 608. In other words, the first adhesive is positioned between the sensor 608 and the membrane 604. The second adhesive 612 attaches the membrane 604 and the clothing 610. In other words, the second adhesive is positioned between the membrane 604 and the clothing 610. When worn by the user 106a, the clothing 610 is positioned proximate the skin 602 of the user 106a. In other words, the sensor 608 is exposed or located on an exterior side of the clothing 610 when the clothing 610 is worn by the user 106a.

The sensors 608 (e.g., and the sensor 304 of FIGS. 3A-3E and/or the sensor 404 of FIGS. 4A-4E) can be various types of sensors (e.g., strain sensors). For example, the sensors 608 of FIGS. 6A-6D FIG. 6 (e.g., and the sensors 304 of FIGS. 3A-3E and/or the sensors 404 of FIGS. 4A-4E) can include, but are not limited to, a load cell sensor, piezoelectric devices or sensors, flexible circuit boards, conductive materials including carbon nanomaterials (e.g., carbon blacks [CBs], carbon nanotubes [CNTs], graphene and its derivatives), metal nanowires (NWs), nanofibers (NFs), and nanoparticles (NPs), MXenes (e.g., Ti3C2Tx), ionic liquid, hybrid micro-/nanostructures, conductive polymers, and/or any other strain and/or stress sensing material(s) or sensor(s) that can generate output signals (e.g., electrical signals, the limb sensor outputs 120) when flexed, bent, and/or otherwise distorted.

The membrane 604 (e.g., and the membrane 302 of FIGS. 3A-3E and/or the membrane 402 of FIGS. 4A-4E) can be formed of various types of materials including, but not limited to, silicone elastomers (e.g., ecfoex and polydimethylsilowane [PDMS]), rubbers, thermoplastic polymers, medical adhesive films, thermoplastic polyurethane (TPU), polystyrene-based elastomers, PDMS, natural fiber-based materials such as cotton, wool, flax, and/or any other material(s) having flexible characteristics.

The membrane sensor 200, 300, 400, and 600a-600d can have various thicknesses in a z-direction (e.g., stack-up direction/cross-section). In some examples, a thickness of the membrane 302, 402 and/or 604 can be the same or different than as a thickness of the sensor 304, 404 and/or 606. The membrane sensor 200, 300, 400 and/or 600a-d, the membrane 302, 402, 604, and/or the sensor 304, 404, 608 can be formed via molding (e.g., injection molding), additive manufacturing (e.g., 3D-printing), lithography, a combination thereof, and/or any other manufacturing process(es).

Figure 7A:
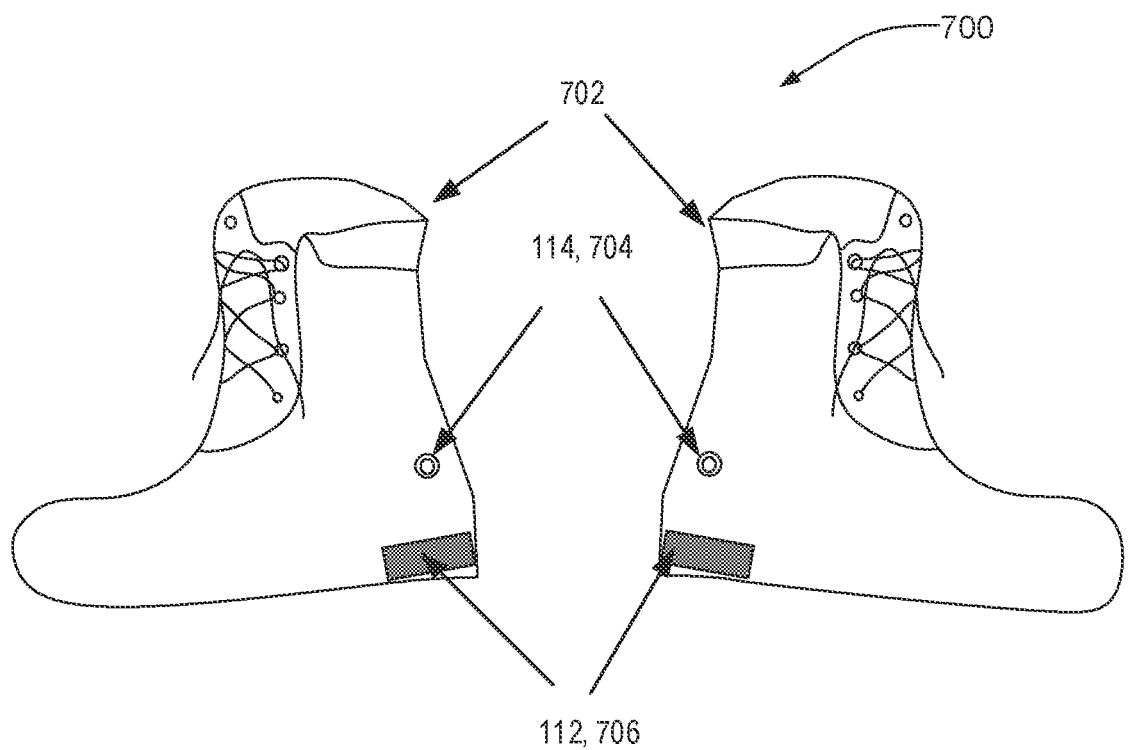
FIG. 7A is an example lower body sensor system of the example ergonomics improvement system of FIG. 1.

FIG. 7A is an example lower body sensor system 700 disclosed herein that can be used to implement the example ergonomics improvement system 100 of FIG. 1. The lower body sensor system 700 of the illustrated example implements the load sensor 112 and the position sensor 114 of FIG. 1. The load sensor 112 includes load cells 706 and the position sensor 114 includes Light Detection and Ranging (LiDAR) sensors 704 (e.g., a pressure pad, step scan sensor, etc.). The load cells 706 and the LiDAR sensors 704 are incorporated (e.g., carried by, attached, or otherwise embedded) in a pair of shoes 702 to be worn by the user 106a. To detect position of the user's feet, the LiDAR sensors 704 emits pulsed waves into a surrounding environment. When the user stands with his feet together, the pulses bounce off the opposing shoe and return to the sensor. The sensor uses a time differential for each pulse to return to the sensor to calculate a distance traveled. When a first foot is forward and/or rearward of the other foot, the pulsed waves project into the surrounding environment instead of an otherwise opposing shoe, indicating that the user's feet are spread apart. Thus, pulses emitted by the LiDAR sensors 704 can be used to determine if the user 106a is standing in a stable or bracing position (e.g., with one foot spaced apart and in front of their other foot) or a non-stable or non-bracing position (e.g., a user standing with their feet spaced apart, but the left foot substantially in line with the right foot) when performing the physical tasks.

Figure 7B:
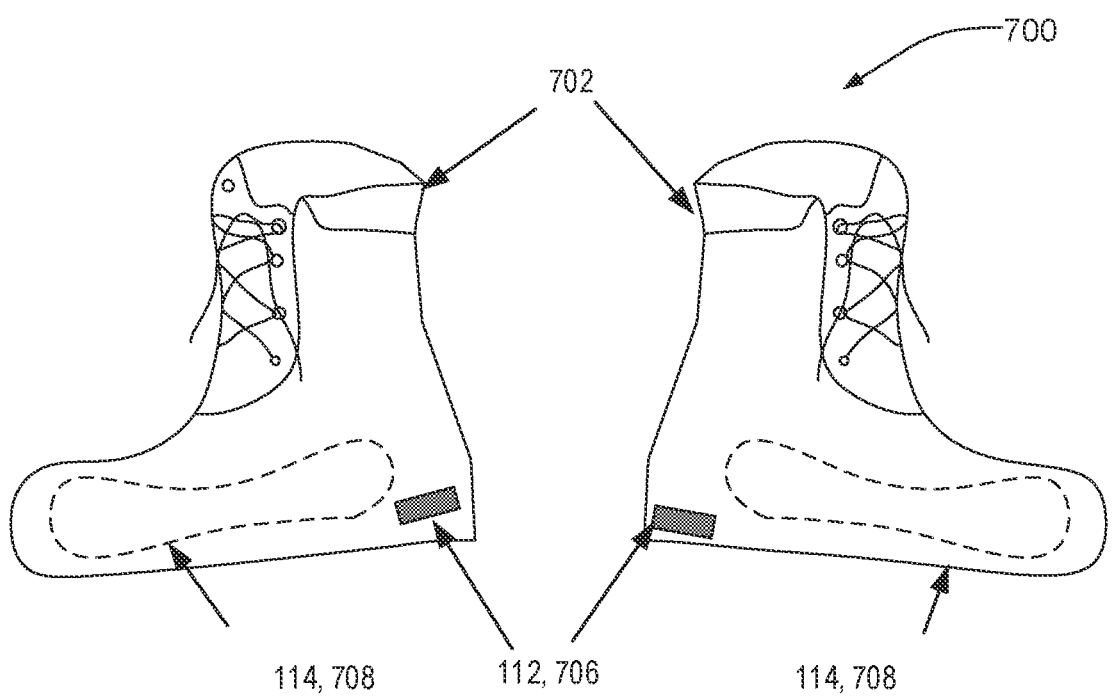
FIG. 7B is another example lower body sensor system disclosed herein that can be used to implement the example ergonomics improvement system of FIG. 1.

FIG. 7B is another example lower body sensor system 700 of the example ergonomics improvement system 100 of FIG. 1. The lower body sensor system 700 of the illustrated example implements the load sensor 112 and the position sensor 114 of FIG. 1. The load sensor 112 includes load cells 706 and the position sensor 114 includes pressure sensors 708 (e.g., a pressure pad, step scan sensor, etc.). The load cells 706 and the pressure sensors 708 are located in (e.g., embedded in the soles of) a pair of shoes 702 that can be worn by the user 106*a* (FIG. 1). The load cells 706 measure a load or weight of the user 106*a* to determine an amount of weight that the user 106*a* is holding or lifting. The pressure sensors 708 of the illustrated example can detect and/or determine a stance (e.g., feet positioning) of the user 106*a* performing a physical task. For example, the pressure sensors 708 can detect and/or otherwise determine if a user is standing in a stable or bracing position (e.g., with one weight evenly distributed in the feet) or a non-stable or non-bracing position (e.g., a user standing with their weight all centered forward on the toes or all centered backwards on the heels) when performing a physical task. In some examples, the pressure sensors 708 can be used to determine weight distribution of the user (e.g., whether the weight distribution is centered). For example, a weight of the user 106*a* being offset toward the heels of the user 106*a* can indicate that the user 106*a* is off-balance and/or at risk of falling or being injured. In some examples, by determining a position of the arm 102*a* via the upper body sensor systems 111*a*, the position of each foot of the user 106*a* via the position sensor 114 and a load carried by the user 106*a* via the load sensor 112, the ergonomics improvement system 100 can determine if the user's stance is stable (e.g., or optimal) for carrying a detected load (e.g., the object 119 of FIG. 1).

Figure 8B:
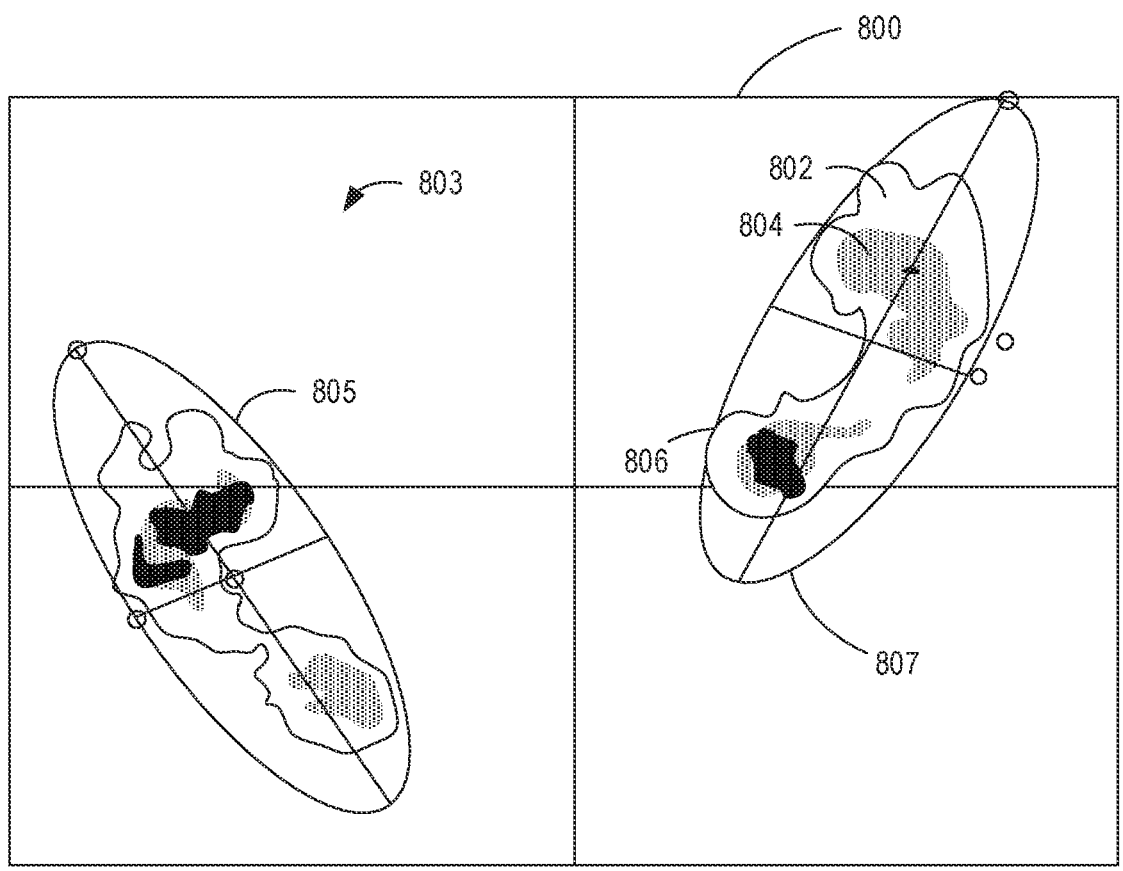

FIGS. 8A and 8B are schematic illustrations of example third outputs 800 of the example lower body sensor system 700 of FIG. 7A. FIG. 8A illustrates a first one 801 of the third outputs 800 and FIG. 8B illustrates a second one 803 of the third outputs 800. For example, the first one 801 of the third outputs 800 is representative of the user 106*a* having his/her feet spaced apart, but a left foot 805 substantially even with a right foot 807. The second one 803 of the third outputs 800 of FIG. 8B is representative of the user 106*a* having the right foot 807 spaced apart and in front of the left foot 805. The pressure sensors 708 generate Stepscan or pressure outputs, such as shown in FIGS. 8A and 8B. The third outputs 800 of the pressure sensors 708 can detect pressure distribution across the feet of the user 106*a*. For example, a white colored area 802 in FIGS. 8A and 8B indicates an area with low pressure, a grey colored area 804 in FIGS. 8A and 8B indicates medium pressure, and a black colored area 806 in FIGS. 8A and 8B indicates high pressure. In FIG. 8A the user has more pressure on his/her right foot 807 as indicated by more grey colored area 804 and more black colored area 806 as compared to the left foot 805, which has more white colored area 802. FIG. 8B illustrates the weight of the user 106*a* concentrated in the back heel of the right foot 807 and concentrated on a pad or middle area of the left foot 805.

Figure 9:
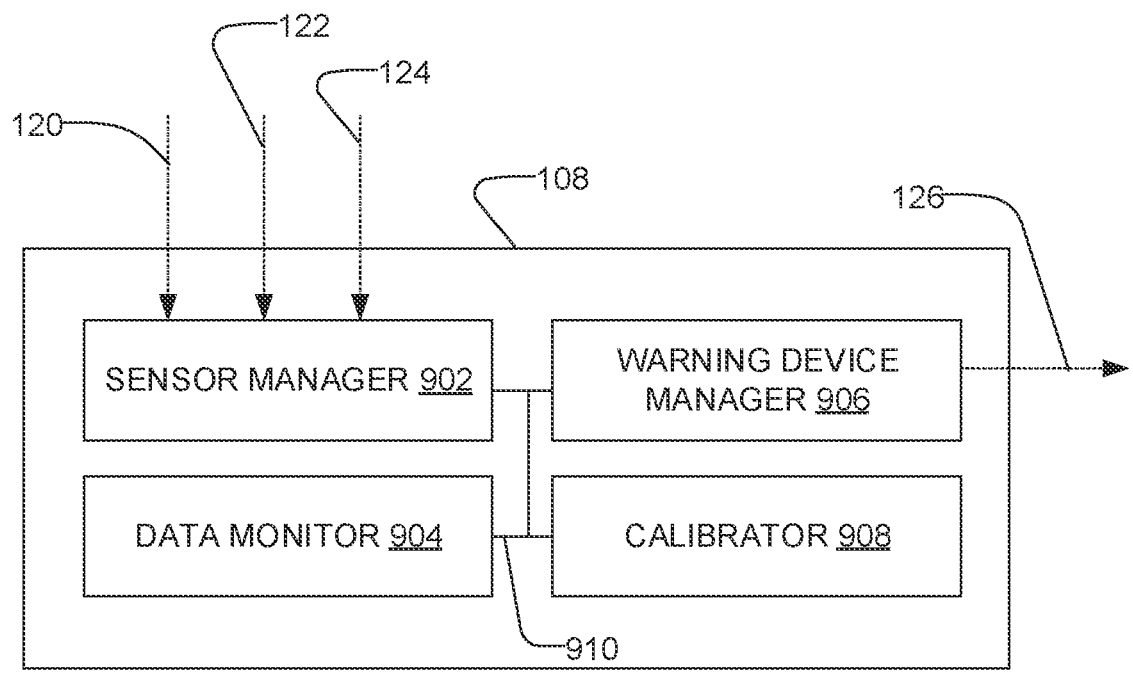
FIG. 9 is a block diagram of an example controller of the example ergonomics improvement system of FIG. 1.

FIG. 9 is a block diagram of the example controller 108 of the example ergonomics improvement system 100 of FIG. 1. The controller 108 includes a sensor manager 902, a data monitor 904, a warning device manager 906, and a calibrator 908. The sensor manager 902, the data monitor 904, the warning device manager 906 and the calibrator 908 are communicatively coupled via a bus 910.

The sensor manager 902 receives inputs from the limb sensor 110, the load sensor 112, or/and the position sensor 114. For example, the sensor manager 902 receives the limb sensor outputs 120, the load sensor outputs 122, and/or the position sensor outputs 124. For example, the sensor manager 902 receives the outputs 205-209, the outputs from the load cells 706, and the outputs from the pressure sensors 708 and/or the LiDAR sensors 704. The sensor manager 902 receives the outputs as currents, voltages, etc. In some examples, the sensor manager 902 can condition the signals for processing by the data monitor 904. In some examples, the sensor manager 902 converts the inputs to binary values (e.g., on/off), digital values, and/or an analog values. For example, the sensor manager 902 can convert the signals of the position sensor 114 to binary values.

For example, the sensor manager 902 can provide binary values "1" for respective ones of the outputs 205-209 of the in response to the output signals not exceeding a threshold value (e.g., an electric current) associated with the respective ones of the membrane sensors 214, 216, 218 and can provide binary values "0" for respective ones of the outputs 205-209 of the membrane sensors 214, 216, 218 in response to the output signals exceeding a threshold value (e.g. an electric current) associated with the respective ones of the membrane sensors 214, 216, 218. For example, the sensor manager 902 can provide a binary value "1" when the position sensor 114 provides signals representative of the user 106*a* being in the stable stance and a binary value "0" when the position sensor 114 provides signals representative of the user 106*a* being in a non-stable stance. In some examples, the sensor manager 902 can provide a binary value "1" in response to the load sensor 112 providing a signal representative of a weight that is greater than a threshold (e.g., 50 pounds) and a binary value "0" in response to the load sensor 112 providing a signal representative of a weight being less than the threshold.

The data monitor 904 stores and processes the signal(s) from the sensor manager 902. The data monitor 904 can compare signal(s) from the sensor manager 902 to a threshold. In some examples, the threshold can be obtained, retrieved or otherwise accessed from memory by the data monitor 904. For example, the data monitor 904, via a comparator, can compare the signals from the sensor manager 902 to a table to determine if the user 106*a* is performing a non-ergonomic or improper activity based on the data provided by the limb sensor outputs 120, the load sensor outputs 122, and/or the position sensor outputs 124. For example, data monitor 904 can compare the signals from the sensor manager 902 to threshold values stored in a look-up table associated with respective thresholds for the respective ones of the limb sensor outputs 120, the load sensor outputs 122 and/or the position sensor output 124. For example, the data monitor 904 can compare a determined position of the limb 102 to a position threshold associated with a measured load carried by the user 106*a* provided by the load sensor 112 and a determined position of the right foot 807 relative to the left foot 805. The data monitor 904 can communicate a warning activation signal to the warning device manager 906 in response to determining that the detected position of the limb 102 exceeds a position threshold (e.g., from a look-up table) associated with or corresponding to the measured load from the load sensor 112 and/or the detected position of the right foot 807 relative to the left foot 805. For example, the outputs 205-209 of FIG. 13 can be indicative of non-ergonomic or improper movement or position of the limb 102 if a load carried by the user 106*a* exceeds a threshold load and/or a stance of the user 106*a* is a non-stable stance (e.g., a stance shown in FIG. 8A). In some instances, the outputs 205-209 of FIG. 13 can be indicative of ergonomic or proper movement or position of a limb 102 if a load carried by the user 106a does not exceed a threshold load and/or a stance of the user 106a is a stable stance (e.g., a stance shown in FIG. 8B).

For example, the look-up table can have a plurality of first threshold values corresponding to outputs from the membrane sensors 214, 216, 218. Based on a comparison of the outputs from the membrane sensors 214, 216, 218 and the thresholds corresponding to the respective ones of the membrane sensors 214, 216, 218 stored in the lookup table, the weight provided by the load sensor 112, and the feet stance provided by the position sensor 114, the data monitor 904 determines if the user 106a is conducting activity (e.g., based on limb movement or position) that is ergonomically proper or ergonomically improper. If one or more signals or a combination of signals from the sensor manager 902 exceeds one or more thresholds or a combination of thresholds compared to the limb sensor outputs 120, the load sensor outputs 122 and the position sensor outputs 124, then the warning device manager 906 triggers the warning signal 126 to trigger an alarm (e.g., indicative of a non-ergonomic activity or movement).

The warning device manager 906 can receive a signal from the data monitor 904 if the signal from the sensor manager 902 exceeds a threshold. The warning device manager 906 can send the warning signal 126 and/or alarm. Example alarms disclosed herein include, but are not limited to, visual alarms (e.g., a light), audio alarms (e.g., a speaker), haptic feedback, a combination thereof and/or any other alarm(s).

The calibrator 908 instructs users of motions to complete calibration such as those illustrated in FIG. 12. The calibrator 908 also stores movement data from various positions from the calibration and can process the movement data to be used as thresholds for the data monitor 904. The calibrator 908 sets a zero or reference value for the limb sensor 110, the load sensor 112 and the position sensor 114.

Alternatively, the controller 108 of the illustrated example can be configured to communicate the sensor outputs (e.g., the sensor outputs 120, 122, 124, 205-209, 800 etc.) from the upper body sensor system 111a and/or the lower body sensor system 111b to a remote electronic device such as, for example, a server, a computer, a control room, a mobile device, a mobile phone, and/or any other computing device communicatively coupled to the controller 108 of the ergonomics improvement system 100. For example, the controller 108 and/or the sensor manager 902 can transmit or communicate one or more outputs provided by the sensors (e.g., the limb sensor 110, the load sensor 112, the position sensor 114, the membrane sensors 214, 216, 218, the load cells 706, the pressure sensors 708, the LiDAR sensors 704 and/or any other sensor(s)). The remote electronic device can be configured to model the movement of the user 106a (e.g., the arm 102a of the user 106a) based on the data provided by the controller 108. The remote electronic device can be configured to detect whether the model represents movements that can be indicative of movements that can be ergonomic or acceptable, or movements that can be non-ergonomic or not acceptable. If the remote electronic device determines that the movements of the user 106a are acceptable, the remote electronic device does not communicate with the controller 108. If the remote electronic device determines that the movements of the user 106a are not acceptable, the remote electronic device communicate instructions to the controller 108 to cause the warning device manager 906 to initiate the warning signal 126 to active the warning device 116.

While an example manner of implementing the controller 108 of FIG. 1 is illustrated in FIG. 9, one or more of the elements, processes and/or devices illustrated in FIG. 9 may be combined, divided, re-arranged, omitted, eliminated and/or implemented in any other way. Further, the sensor manager 902, the data monitor 904, the warning device manager 906, and the calibrator 908 and/or, more generally, the example controller of FIG. 1 may be implemented by hardware, software, firmware and/or any combination of hardware, software and/or firmware. Thus, for example, any of the sensor manager 902, the data monitor 904, the warning device manager 906, and the calibrator 908 and/or, more generally, the example controller 108 of FIG. 1 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the sensor manager 902, the data monitor 904, the warning device manager 906, and the calibrator 908 and/or, more generally, the example controller 108 of FIG. 1 is/are hereby expressly defined to include a non-transitory computer readable storage device or storage disk such as a memory, a digital versatile disk (DVD), a compact disk (CD), a Blu-ray disk, etc. including the software and/or firmware. Further still, the example controller 108 of FIG. 1 may include one or more elements, processes and/or devices in addition to, or instead of, those illustrated in FIG. 9, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 10:
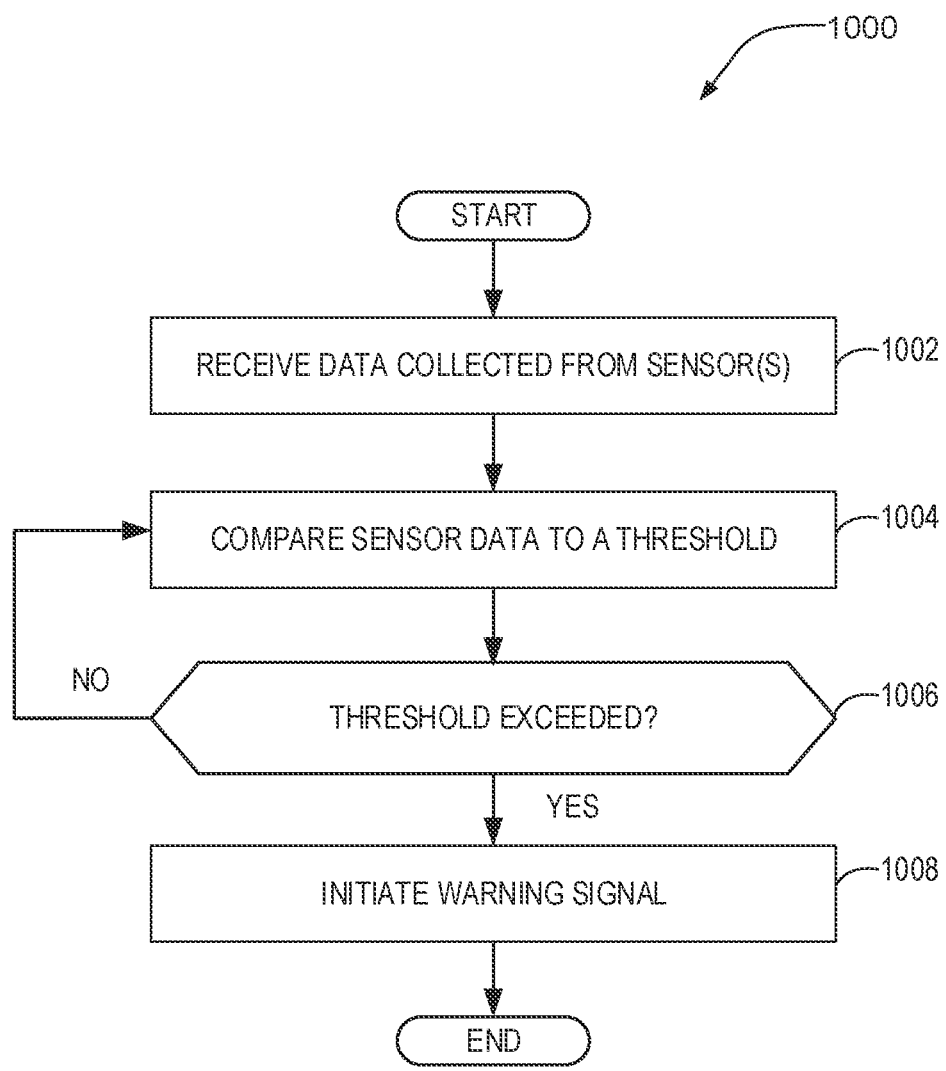
FIG. 10 is an example of a flowchart representative of an example method that can be performed by the example controller of FIG. 9 of the example ergonomics improvement system of FIG. 1.
Figure 11:
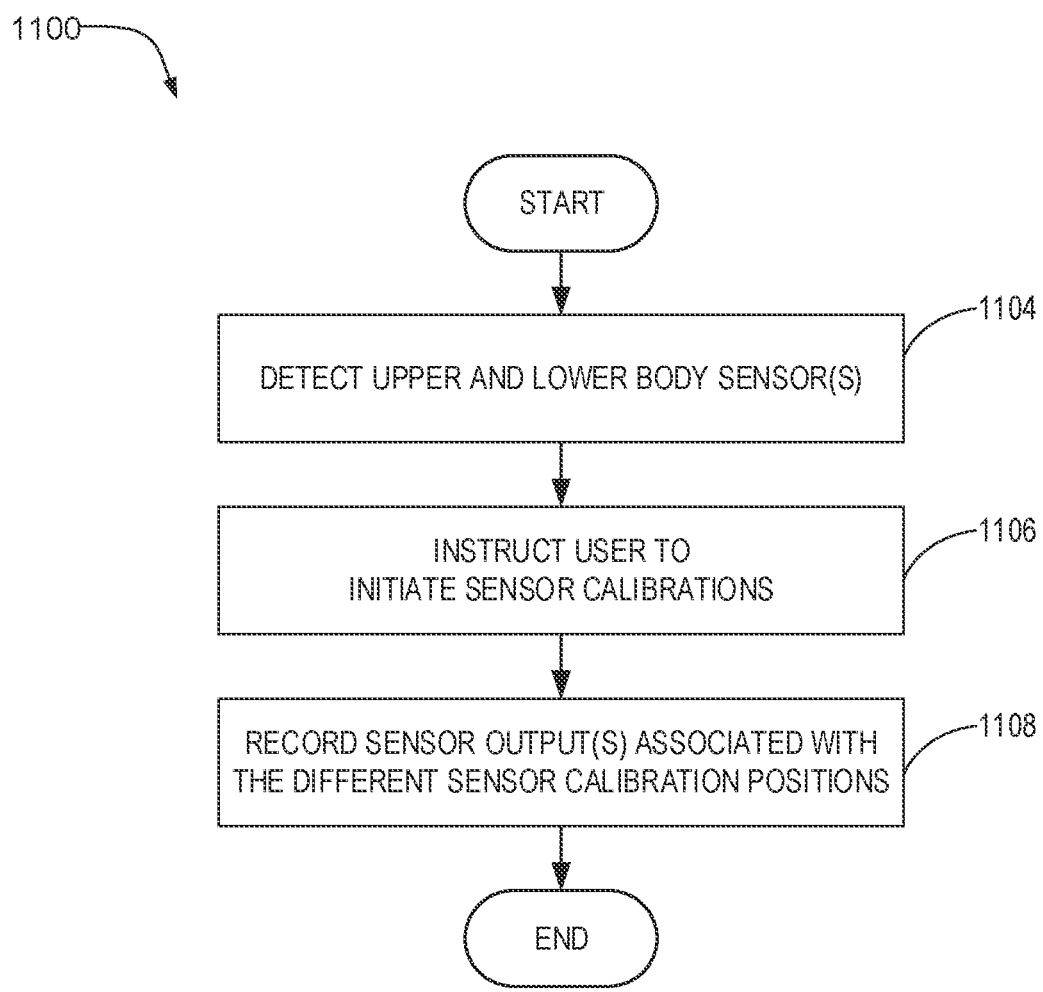
FIG. 11 is an example of a flowchart representative of an example method to calibrate example upper body sensor system of the example ergonomics improvement system of FIG. 1.

A flowchart representative of example hardware logic, machine readable instructions, hardware implemented state machines, and/or any combination thereof for implementing the ergonomics improvement system 100 of FIG. 1 is shown in FIG. 10 and FIG. 11. The machine readable instructions may be one or more executable programs or portion(s) of an executable program for execution by a computer processor such as the processor 1312 shown in the example processor platform 1300 discussed below in connection with FIG. 1. The program may be embodied in software stored on a non-transitory computer readable storage medium such as a CD-ROM, a floppy disk, a hard drive, a DVD, a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowcharts illustrated in FIG. 10 and FIG. 11, many other methods of implementing the example ergonomics improvement system 100 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an FPGA, an ASIC, a comparator, an operationalamplifier (op-amp), a logic circuit, etc.) structured to perform the corresponding operation without executing software or firmware.

The machine readable instructions described herein may be stored in one or more of a compressed format, an encrypted format, a fragmented format, a compiled format, an executable format, a packaged format, etc. Machine readable instructions as described herein may be stored as data (e.g., portions of instructions, code, representations of code, etc.) that may be utilized to create, manufacture, and/or produce machine executable instructions. For example, the machine readable instructions may be fragmented and stored on one or more storage devices and/or computing devices (e.g., servers). The machine readable instructions may require one or more of installation, modification, adaptation, updating, combining, supplementing, configuring, decryption, decompression, unpacking, distribution, reassignment, compilation, etc. in order to make them directly readable, interpretable, and/or executable by a computing device and/or other machine. For example, the machine readable instructions may be stored in multiple parts, which are individually compressed, encrypted, and stored on separate computing devices, wherein the parts when decrypted, decompressed, and combined form a set of executable instructions that implement a program such as that described herein.

In another example, the machine readable instructions may be stored in a state in which they may be read by a computer, but require addition of a library (e.g., a dynamic link library (DLL)), a software development kit (SDK), an application programming interface (API), etc. in order to execute the instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, the disclosed machine readable instructions and/or corresponding program(s) are intended to encompass such machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example processes of FIG. 10 and FIG. 11 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The method 1000 of FIG. 10 is an example method for implementing the ergonomics improvement system 100 of FIG. 1. The method 1000 begins at block 1002, with the sensor manager 902 receiving data collected from sensor(s). The sensor(s) can include the limb sensor 110, the load sensor 112, the position sensor 114, the membrane sensors 214, 216, 218, the load cells 706, the pressure sensor 708, the LiDAR sensors 704 and/or any other sensor(s).

At block 1004, the data monitor 904 compares data (e.g., signals(s)) from the sensor manager 902 data to a threshold. The threshold can be obtained from a lookup table that can be stored in a database or memory of the controller 108.

At block 1006, the data monitor 904 determines whether the threshold at block 1004 is exceeded. If the data monitor 904 determines that the threshold is exceeded at block 1006, then the process continues to block 1008. At block 1008, the warning device manager 906 initiates a warning signal (e.g., the warning signal 126) to activate the alarm and/or warning device 116. If the data monitor 904 determines at block 1006 that the threshold is not exceeded, then the process returns to block 1002.

Referring to FIG. 11, the method 1100 is an example method to calibrate the upper body sensor system 111*a* and the lower body sensor system 111*b* of the example ergonomics improvement system 100 of FIG. 1. For example, calibration can be implemented using the calibrator 908. For example, calibration of the example ergonomics improvement system 100 of FIG. 1 can occur when the system is initially turned on and/or at any other time when the system is in use. In some examples, calibration can be automatically set to occur at pre-defined intervals or at certain events such as when the controller 108 detects outlier values outputted by one or more sensors of the ergonomics improvement system of FIG. 1.

At block 1102, the example ergonomics improvement system 100 of FIG. 1 can detect the upper body sensor system 111*a* (e.g., the membrane sensors 214, 216, 218) and the lower body sensor system 111*b* (e.g., the load cells 706, the pressure sensor 708, the LiDAR sensor 704, etc.) via the sensor manager 902. At block 1104, the example calibrator 908 instructs the user 106*a* to initiate sensor calibrations. Example sensor calibration positions are disclosed herein and are illustrated and discussed in FIG. 12.

At block 1106, the example calibrator 908 records sensor output(s) associated with the different sensor calibrations. For example, the calibrated values for each of the sensors (e.g., the limb sensor 110, the load sensor 112, and/or the position sensor 114) are zero values or reference values.

FIG. 12 is an example diagram representative of example calibration positions 1200 disclosed herein that can be used to implement the example method 1100 of FIG. 11. The sensor calibration positions can be instructed to the user 106*a* using a user interface that can include, for example, a display, a speaker, a combination thereof, and/or any other communication device carried by the controller 108. The example calibration positions 1200 can be used to calibrate one or more of the membrane sensors 214, 216, 218 after the sensors are carried or coupled to the user 106*a*. For example, each of the membrane sensors 214, 216, 218 can be calibrated using the example calibration positions 1200 of FIG. 12. For example, the calibration positions 1200 include three sets of calibration positions (i.e., position 1, position 2, position 3) for each of the shoulder 208, the elbow 206 and the hand/wrist 202. However, the calibration positions are not limited to the positions shown in FIG. 12 and can include one or more other positions that are not shown in FIG. 12.

In position 1 of a shoulder calibration 1202, the user 106*a* is instructed to move their arms (i.e., the arm 102*a*) in a forward position (e.g., a fully forward extended position in a direction in front of the user 106*a*) and rearward position (e.g., a fully rearward extended position in a direction behind the user 106*a*). The controller 108 records outputs of the sensors (e.g., the membrane sensors 214, 216, 218) when the arm 102*a* moves to the forward position and the rearward position.

In position 2 of a shoulder calibration 1204, the user 106*a* is instructed to move their arms in an upward position (e.g., a fully raised position above the user's head) and downward position (e.g., a fully extended position on the side of the user's body). The controller 108 records outputs of the sensors (e.g., the membrane sensors 214, 216, 218) when the arm 102*a* moves to the upward position and the downward position.

In position 3 of a shoulder calibration 1206, the user 106*a* is instructed to extend their arms outwardly and sideways (e.g., a wingspan formation) and rotate/twist their arms in a circular motion between a first rotational position (e.g., twist or rotate in a first rotational position) and a second rotational position (e.g., twist or rotate in a second rotational direction opposite the first direction). The controller 108 records outputs of the sensors (e.g., the membrane sensors 214, 216, 218) when the arm 102*a* moves to the first rotational position and the first rotational position.

In position 1 of an elbow calibration 1208, the user 106*a* is instructed to move their arms sideways and to move their arms to a curled position (e.g., fully curled position where the hand is proximate the shoulder 208) and an extended position (e.g., a fully extended position). The controller 108 records outputs of the sensors (e.g., the membrane sensors 214, 216, 218) associated with the elbow 206 when the arm 102*a* moves to the curled position and the extended position.

In position 2 of an elbow calibration 1210, the user 106*a* is instructed to bend their elbows and move their elbows while in the bent position to a bent upward position and a bent downward position. The controller 108 records outputs of the sensors (e.g., the membrane sensors 214, 216, 218) when the arm 102*a* moves to the bent upward position and the bent downward position.

In position 3 of the elbow calibration 1212, the user 106*a* is instructed to rotate their arms with the elbow bent between a first rotational position and a second rotational position opposite the first rotational position. The controller 108 records outputs of the sensors (e.g., the membrane sensors 214, 216, 218) when the arm 102*a*, with the bent elbow 206, moves to the first rotational position and the second rotational position.

In position 1 of a wrist/hand calibration 1214, the user 106*a* is instructed to move or bend their hand about the wrist to an upward position (e.g., fully upward position) and a downward position (e.g., a fully downward position). The controller 108 records outputs of the sensors (e.g., the membrane sensors 214, 216, 218) when the hand moves to the first rotational position and the second rotational position.

In position 2 of a wrist/hand calibration 1216, the user 106*a* is instructed to move their hand sideways about the wrist to a first side position (e.g., fully right side position) and a second side position (e.g., a fully left side position). The controller 108 records outputs of the sensors (e.g., the membrane sensors 214, 216, 218) when the hand moves to the first side position and the second side position.

In position 3 of a wrist/hand calibration 1218, the user 106*a* is instructed to twist their hand sideways about the wrist to a first rotational position (e.g., a fully rotational position in a first rotational direction) and a second rotational position (e.g., a fully rotational position in a second rotational direction). The controller 108 records outputs of the sensors (e.g., the membrane sensors 214, 216, 218) when the hand moves to the first rotational position and the second rotational position.

Figure 13:
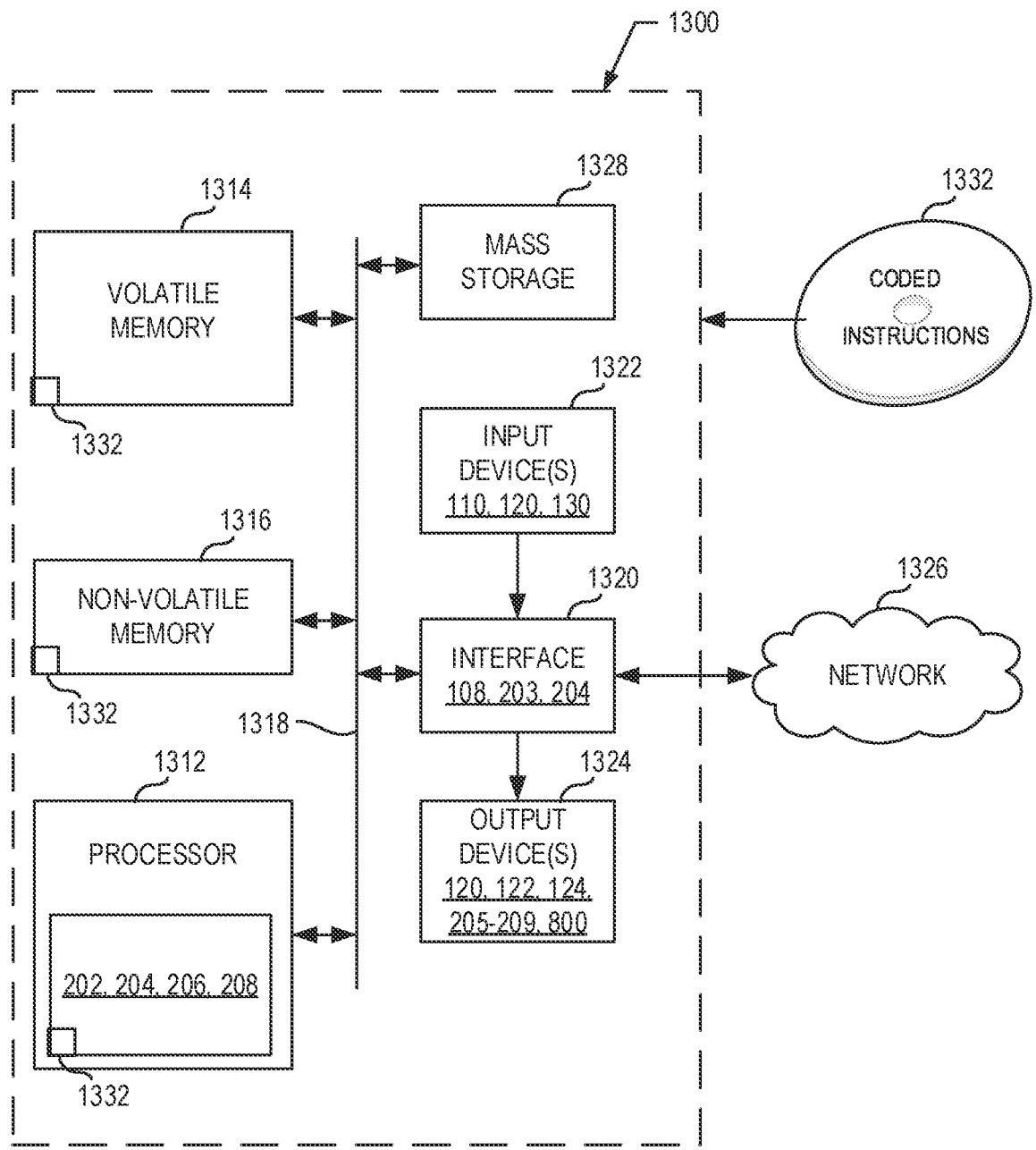
FIG. 13 is a block diagram of an example processing platform structured to execute the instructions of FIGS. 10 and 11 to implement an example controller of the example ergonomics improvement systems disclosed herein.

FIG. 13 is a block diagram of an example processing platform structured to execute instructions of FIGS. 10 and 11 to implement an example controller of example ergonomics improvement systems disclosed herein.

FIG. 13 is a block diagram of an example processor platform 1300 structured to execute the instructions of FIG. 10 and FIG. 11 to implement the ergonomics improvement system 100 of FIG. 1. The processor platform 1300 can be, for example, a server, a personal computer, a workstation, a self-learning machine (e.g., a neural network), a mobile device (e.g., a cell phone, a smart phone, a tablet such as an iPad™, a headset or other wearable device, or any other type of computing device.

The processor platform 1300 of the illustrated example includes a processor 1312. The processor 1312 of the illustrated example is hardware. For example, the processor 1312 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the sensor manager 902, the data monitor 904, the warning device manager 906 and the calibrator 908.

The processor 1312 of the illustrated example includes a local memory 1313 (e.g., a cache). The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1316 may be implemented by flash memory and/or any other desired type of memory device. Access to the volatile memory 1314 and the non-volatile memory 1316 is controlled by a memory controller.

The processor platform 1300 of the illustrated example also includes an interface circuit 1320. The interface circuit 1320 may be implemented by any type of interface standard, such as an Ethernet interface, a universal serial bus (USB), a Bluetooth® interface, a near field communication (NFC) interface, and/or a PCI express interface.

In the illustrated example, one or more input devices 1322 are connected to the interface circuit 1320. The input device(s) 1322 permit(s) a user to enter data and/or commands into the processor 1312. The input device(s) can be implemented by, for example, an audio sensor, a microphone, a camera (still or video), a keyboard, a button, a mouse, a touchscreen, and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), and/or speaker. The interface circuit 1320 of the illustrated example, thus, typically includes a graphics driver card, a graphics driver chip and/or a graphics driver processor.

The interface circuit 1320 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1326. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, redundant array of independent disks (RAID) systems, and digital versatile disk (DVD) drives.

The machine executable instructions 1332 of FIG. 10 and FIG. 11 may be stored in the mass storage device 1328, in the volatile memory 1014, in the non-volatile memory 1316, and/or on a removable non-transitory computer readable storage medium such as a CD or DVD.

The foregoing examples of the ergonomics improvement systems can be wearable devices. Although each example ergonomics improvement systems disclosed above have certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features. For example, the first membrane sensor 214 can be implemented by the membrane sensor 300, the second membrane sensor 216 can be implemented by the membrane sensor 400, the third membrane sensor can be implemented by any one of the membrane sensors 600a-d, and/or any combination thereof.

Further, the disclosure comprise examples according to the following clauses:

1. A wearable ergonomics improvement system includes a membrane including a first frame having a plurality of first cutouts defining a first pattern, and a sensor coupled to the membrane, the sensor including a second frame having a plurality of second cutouts defining a second pattern, the first pattern being complementary to the second pattern.
2. The system of any preceding clause, wherein the first pattern and the second pattern are Kirigami patterns.
3. The system of any preceding clause, wherein the first pattern and the second pattern are Auxetic patterns.
4. The system of any preceding clause, wherein the sensor is strain sensor.
5. The system of any preceding clause, wherein the strain sensor is a flex circuit.
6. The system of any preceding clause, wherein the sensor is a piezoelectric sensor.
7. The system of any preceding clause, wherein the membrane is composed of at least one of a Kirigami pattern or a Auxetic pattern.
8. The system of any preceding clause, further including an adhesive to couple the membrane and the sensor.
9. A wearable ergonomics improvement system comprising: a first membrane sensor to couple to a shoulder of the body, the first membrane to generate first outputs in response to movement of the shoulder to detect at least one of a position or rotation of the shoulder, a second membrane sensor to couple to an elbow of the body, the second membrane sensor to generate second outputs in response to movement of the elbow to detect at least one of a position or rotation of the elbow, and a third membrane system to couple to a wrist of the body, a third membrane sensor to generate third outputs in response to movement of a hand to detect at least one of a position or rotation of the hand.
10. The system of any preceding clause, wherein each of the first membrane sensor, the second membrane sensor, and the third membrane sensor includes a plurality of openings defining a pattern.
11. The system of any preceding clause, wherein the pattern is at least one of a Kirigami pattern or an Auxetic pattern.

12. The system of any preceding clause, further including a load sensor to measure a load of the body.
13. The system of any preceding clause, further including a position sensor to detect a position of a right foot of a body relative to a left foot of the body.
14. The system of any preceding clause, wherein a load sensor and a position sensor are positioned in footwear to be worn by a user.
15. The system of any preceding clause, further comprising a processor to: determine a position of a limb relative to the body based on first outputs of a first membrane sensor, second outputs of the second membrane sensor, and third outputs of the third membrane sensor, determine a measured load based on a fourth output from the load sensor, determine a position of a right foot of the body relative to a left foot of the body based on a fifth output of the position, compare the determined position of the limb to a position threshold associated with measured load and the detected position of the right foot relative to the left foot, and generate a warning signal in response to determining that the detected position exceeds the position threshold associated with the measured load and the detected position of the right foot relative to the left foot.
16. The system of any preceding clause, wherein the load sensor includes a load cell.
17. The system of any preceding clause, wherein the position sensor includes at least one of a pressure sensor or a LiDAR sensor.
18. A method for tracking movement of a limb of a body, the method comprising: determining a position of the limb relative to the body based on first outputs of a first membrane sensor, second outputs of the second membrane sensor, and third outputs of the third membrane sensor, determining a position of the limb relative to the body based on first, second, or third outputs received, receiving a second output from a load sensor carried by the body, determining a load of the body based on the received second output, receiving third outputs from a step scanner carried by the body, determining a foot position by detecting a position of a left foot of the body relative to a position of a right foot of the body based on the third outputs from a pressure sensor, comparing the determined position of the limb and a position threshold associated with the determined load and the determined foot position, determining if the determined position exceeds the position threshold, and generating a warning signal if the determined position exceeds the position threshold.
19. The system of any preceding clause, wherein the generating of the warning signal includes generating at least one of a sound signal, a haptic signal, or a light signal.
20. The system of any preceding clause, further including retrieving the position threshold from a look-up table.

What is claimed is:
1. A wearable ergonomics improvement system comprising:
   a first membrane sensor to couple to a shoulder of a body, the first membrane sensor to generate first outputs in response to movement of the shoulder to detect at least one of a position or rotation of the shoulder, the first membrane including:
      a first sensor frame providing a first layer including a first material, the first sensor frame having a plurality of first cutouts; and
      a first membrane frame providing a second layer including a second material different than the first material, the first membrane frame to carry the first sensor frame, the first membrane frame having a plurality of second cutouts, the first sensor frame to overlay to first membrane frame, the first cutouts complementary to the second cutouts;
   a second membrane sensor to couple to an elbow of the body, the second membrane sensor to generate second outputs in response to movement of the elbow to detect at least one of a position or rotation of the elbow, the second membrane sensor including:
      a second sensor frame providing a third layer including a third material, the second sensor frame having a plurality of third cutouts; and
      a second membrane frame providing a fourth layer including a fourth material different than the third material, the second membrane frame having a plurality of fourth cutouts, the second sensor frame to overlay the second membrane frame, the third cutouts complementary to the fourth cutouts; and
   a third membrane sensor to couple to a wrist of the body, the third membrane sensor to generate third outputs in response to movement of a hand to detect at least one of a position or rotation of the hand, the third membrane sensor including:
      a third sensor frame providing a fifth layer including a fifth material, the third sensor frame having a plurality of fifth cutouts; and
      a third membrane frame providing a sixth layer including a sixth material different than the fifth material, the third membrane frame having a plurality of sixth cutouts, the third sensor frame to overlay the third membrane frame, the fifth cutouts complementary to the sixth cutouts.
2. The system of claim 1, further including a load sensor to measure a load of the body.
3. The system of claim 1, further including a position sensor to detect a position of a right foot of the body relative to a left foot of the body.
4. The system of claim 1, further including a load sensor and a position sensor in footwear to be worn on the body.
5. The system of claim 4, further comprising a processor to:
   determine a position of a limb relative to the body based on the first outputs of the first membrane sensor, the second outputs of the second membrane sensor, and the third outputs of the third membrane sensor;
   determine a measured load based on a fourth output from the load sensor;
   detect a position of a right foot of the body relative to a left foot of the body based on a fifth output of the position sensor;
   compare the determined position of the limb to a position threshold associated with measured load and the detected position of the right foot relative to the left foot; and
   generate a warning signal in response to determining that the detected position exceeds the position threshold associated with the measured load and the detected position of the right foot relative to the left foot.
6. The system of claim 5, wherein the load sensor includes a load cell.
7. The system of claim 5, wherein the position sensor includes at least one of a pressure sensor or a LiDAR sensor.
8. The system of claim 1, wherein the first membrane sensor, the second membrane sensor, and the third mem- brane sensor include at least one of a strain sensor or a piezoelectric sensor, and wherein the first and second cutouts, the third and fourth cutouts, and the fifth and sixth cutouts form at least one of a Kirigami pattern or an Auxetic pattern.

9. The system of claim 1, wherein the plurality of first cutouts and the plurality of second cutouts define a first pattern, the plurality of third cutouts and the plurality of fourth cutouts define a second pattern, and the plurality of fifth cutouts and the plurality of sixth cutouts define a third pattern.

10. The system of claim 9, wherein at least one of the first pattern, the second pattern or the third pattern is at least one of a Kirigami pattern or an Auxetic pattern.

11. The system of claim 1, wherein the first membrane sensor includes an adhesive to couple the first membrane frame and the first sensor frame.

12. The system of claim 11, wherein the adhesive is a first adhesive, the second membrane sensor further including a second adhesive to couple the second membrane frame and the second sensor frame, and the third membrane sensor further including a third adhesive to couple the third membrane frame and the third sensor frame.

13. The system of claim 1, further including an adhesive layer to couple the first membrane frame and the first sensor frame.

14. The system of claim 1, wherein at least one of the first sensor frame, the second sensor frame or the third sensor frame is a flex circuit.

15. The system of claim 1, wherein at least one of the first sensor frame, the second sensor frame or the third sensor frame includes a piezoelectric sensor.

16. The system of claim 1, wherein the wearable ergonomics improvement system is at least one of a garment or a sleeve.

17. The system of claim 1, wherein the first cutouts align with respective ones of the second cutouts, the third cutouts align with respective ones of the fourth cutouts, and the fifth cutouts align with respective ones of the sixth cutouts.

* * * * *